US012595501B2

(12) United States Patent
Davis et al.

(10) Patent No.: US 12,595,501 B2
(45) Date of Patent: Apr. 7, 2026

(54) EXPRESSION OF PRODUCTS FROM NUCLEIC ACID CONCATEMERS

(71) Applicant: General Electric Company, Schenectady, NY (US)

(72) Inventors: Brian Michael Davis, Niskayuna, NY (US); Erik Leeming Kvam, Niskayuna, NY (US); John Richard Nelson, Clifton Park, NY (US); Lisa Anne Lowery, Niskayuna, NY (US); Wei Gao, Clifton Park, NY (US)

(73) Assignee: GLOBAL LIFE SCIENCES SOLUTIONS USA LLC, Marlborough, MA (US)

( * ) Notice: Subject to any disclaimer, the term of this patent is extended or adjusted under 35 U.S.C. 154(b) by 610 days.

(21) Appl. No.: 16/440,511

(22) Filed: Jun. 13, 2019

(65) Prior Publication Data
US 2020/0392554 A1 Dec. 17, 2020

(51) Int. Cl.
| | |
|---|---|
| *C12P 21/02* | (2006.01) |
| *C12N 7/00* | (2006.01) |
| *C12N 15/10* | (2006.01) |
| *C12N 15/85* | (2006.01) |
| *C12N 15/86* | (2006.01) |
| *C12P 19/34* | (2006.01) |

(52) U.S. Cl.
CPC ............... *C12P 21/02* (2013.01); *C12N 7/00* (2013.01); *C12N 15/1003* (2013.01); *C12N 15/86* (2013.01); *C12P 19/34* (2013.01); *C12N 2015/8518* (2013.01); *C12N 2750/14143* (2013.01)

(58) Field of Classification Search
CPC . C12P 21/02; C12P 19/34; C12N 7/00; C12N 15/1003; C12N 15/86; C12N 2015/8518; C12N 2750/14143
See application file for complete search history.

(56) References Cited

U.S. PATENT DOCUMENTS

| | | |
|---|---|---|
| 5,648,245 A | 7/1997 | Fire et al. |
| 5,807,717 A | 9/1998 | Joyce |
| 6,287,824 B1 | 9/2001 | Lizardi |
| 6,977,153 B2 | 12/2005 | Kumar et al. |
| 7,135,312 B2 | 11/2006 | Kool |
| 7,256,020 B2 | 8/2007 | Lyamichev et al. |
| 7,575,865 B2 | 8/2009 | Leamon et al. |
| 7,897,380 B2 | 3/2011 | Kay et al. |
| 8,715,732 B2 | 5/2014 | Luo et al. |
| 8,921,072 B2 | 12/2014 | Nelson et al. |
| 9,109,250 B2 | 8/2015 | Hill |
| 9,125,845 B2 | 9/2015 | Nelson et al. |
| 9,353,393 B2 | 5/2016 | Nelson et al. |
| 2005/0079510 A1 | 4/2005 | Berka et al. |
| 2008/0153128 A1 | 6/2008 | Kim et al. |
| 2008/0160524 A1 | 7/2008 | Ma et al. |
| 2008/0220425 A1 | 9/2008 | Ma et al. |
| 2008/0305142 A1 | 12/2008 | Chen et al. |
| 2010/0008939 A1 | 1/2010 | Nelson et al. |
| 2017/0321239 A1* | 11/2017 | Nelson ................... C12N 15/67 |

FOREIGN PATENT DOCUMENTS

| | | |
|---|---|---|
| CN | 106086012 A | 11/2016 |
| EP | 1489188 A1 | 12/2004 |
| WO | 2005003389 A2 | 1/2005 |
| WO | 2007/14608 A1 | 12/2007 |
| WO | 2014189768 A1 | 11/2014 |
| WO | 2016034849 A1 | 3/2016 |
| WO | 2017191007 A1 | 11/2017 |
| WO | 2018033730 A1 | 2/2018 |
| WO | 2019/030155 A1 | 2/2019 |
| WO | 2019/053039 A1 | 3/2019 |
| WO | 03072796 A1 | 9/2023 |

OTHER PUBLICATIONS

Celie Phn et al. Recombinant cloning strategies for protein expression. 2016. Current Opinion in Structural Biology. 38:145-154. (Year: 2016).*

Grubaugh, Nathan D., et al.; "Mosquitoes Transmit Unique West Nile Virus Populations during Each Feeding Episode", Cell Reports, vol. 19, Issue: 04, pp. 709-718, Apr. 25, 2017.

Weger-Lucarelli, James, et al.; "Rescue and Characterization of Recombinant Virus from a New World Zika Virus Infectious Clone", Journal of Visualized Experiments, Issue: 124, pp. 01-08, Jun. 7, 2017.

Karbowniczek, Kinga, et al.; "Doggybone™ DNA: an advanced platform for AAV production", Cell & gene therapy insights, pp. 731-738, Nov. 16, 2017.

Aliota, Matthew T., et al.; "Molecularly barcoded Zika virus libraries to probe in vivo evolutionary dynamics", PLOS Pathogens, pp. 01-25, Mar. 28, 2018.

Weger-Lucarelli, James, et al.; "Using barcoded Zika virus to assess virus population structure in vitro and in Aedesaegypti mosquitoes", Virology, vol. 521, pp. 138-148, Jun. 8, 2018.

PCT Search Report for PCT Application No. PC/EP2020/065980 mailed Aug. 3, 2020 (17 pages).

Japanese Office Action for JP Application No. 2018-557422 mailed Nov. 30, 2020 (12 pages with English translation).

(Continued)

*Primary Examiner* — Paul J Holland
(74) *Attorney, Agent, or Firm* — Eversheds-Sutherland (US) LLP

(57) ABSTRACT

Provided are techniques for generating expression products using one or more nucleic acid concatemers that include tandem repeats of a nucleic acid sequence encoding the expression product or products. In one embodiment, different expression products may be co-expressed using a concatemer mixture of a first nucleic acid concatemer and a second nucleic acid concatemer having a predefined ratio to one another.

22 Claims, 14 Drawing Sheets

Specification includes a Sequence Listing.

(56) References Cited

OTHER PUBLICATIONS

Gagoski et al., "Gateway-Compatible Vectors for High-Throughput Protein Expression in Pro- and Eukaryotic Cell-Free Systems," Journal of Biotechnology, 2015, 195:1-7.

Komar et al., "Synonymous Codon Substitutions Affect Ribosome Traffic and Protein Folding During in vitro Translation," FEBS Letters 462, 1999, 387-393.

Sakatani et al., "A Transcription and Translation-Coupled DNA Replication System Using Rolling-Circle Replication," Scientific Reports, 2015, 9 pages.

Kuhn et al., "Rolling-circle amplification under topological constraints", Nucleic Acids Research, vol. 30, Issue 2, pp. 574-580, 2001.

Kumar et al., "Cell-free protein synthesis using multiply-primed rolling circle amplification products", BioTeciniques, vol. 47, Issue 1, pp. 637-639, Jul. 2009.

Carlson et al., "Cell-free protein synthesis: Applications come of age", Biotechnology Advances, 2011.

Kuhn et al., "Rolling-Circle Amplification of Duplex DNA Sequences assisted by PNA Openers," pp. 227-243, https://www.bu.edu/cab/CAB PDF/Kuhn and Emidov DNA Amplification '04.pdf.

Japanese Office Action for JP Application No. 2021-573577, mailed Sep. 30, 2024 (13 pages with English translation).

Karda et al., "Production of lentiviral vectors using novel, enzymatically produced, linear DNA", Gene Therapy, Jan. 2019, vol. 26, p. 86-92.

* cited by examiner

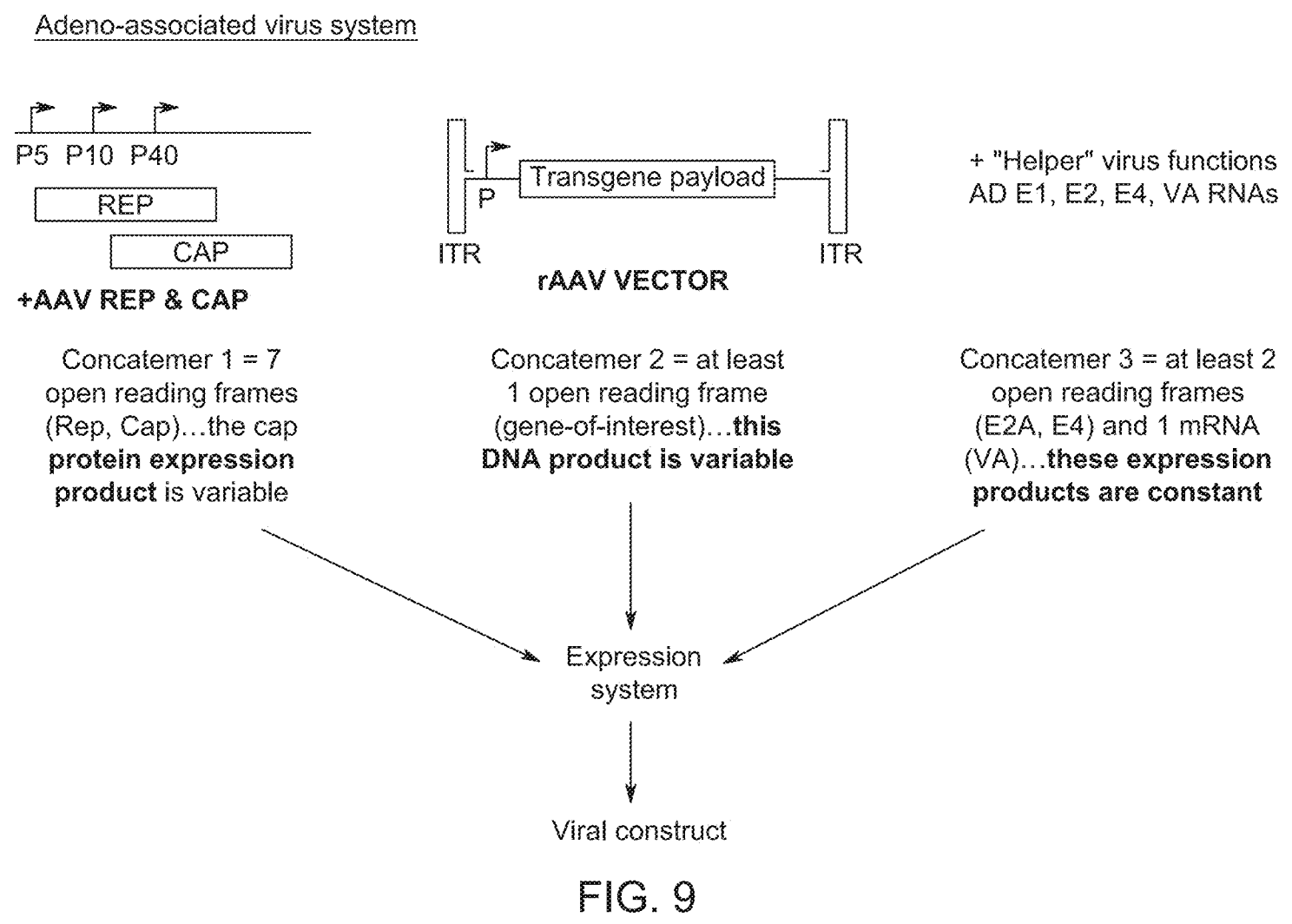

Adeno-associated virus system

P5  P10  P40

REP

CAP

+AAV REP & CAP

Concatemer 1 = 7 open reading frames (Rep, Cap)...the cap protein expression product is variable rAAV VECTOR

ITR

Transgene payload

P

ITR

Concatemer 2 = at least 1 open reading frame (gene-of-interest)...this DNA product is variable + "Helper" virus functions AD E1, E2, E4, VA RNAs Concatemer 3 = at least 2 open reading frames (E2A, E4) and 1 mRNA (VA)...these expression products are constant Expression system Viral construct

FIG. 9

CRISPR gRNA

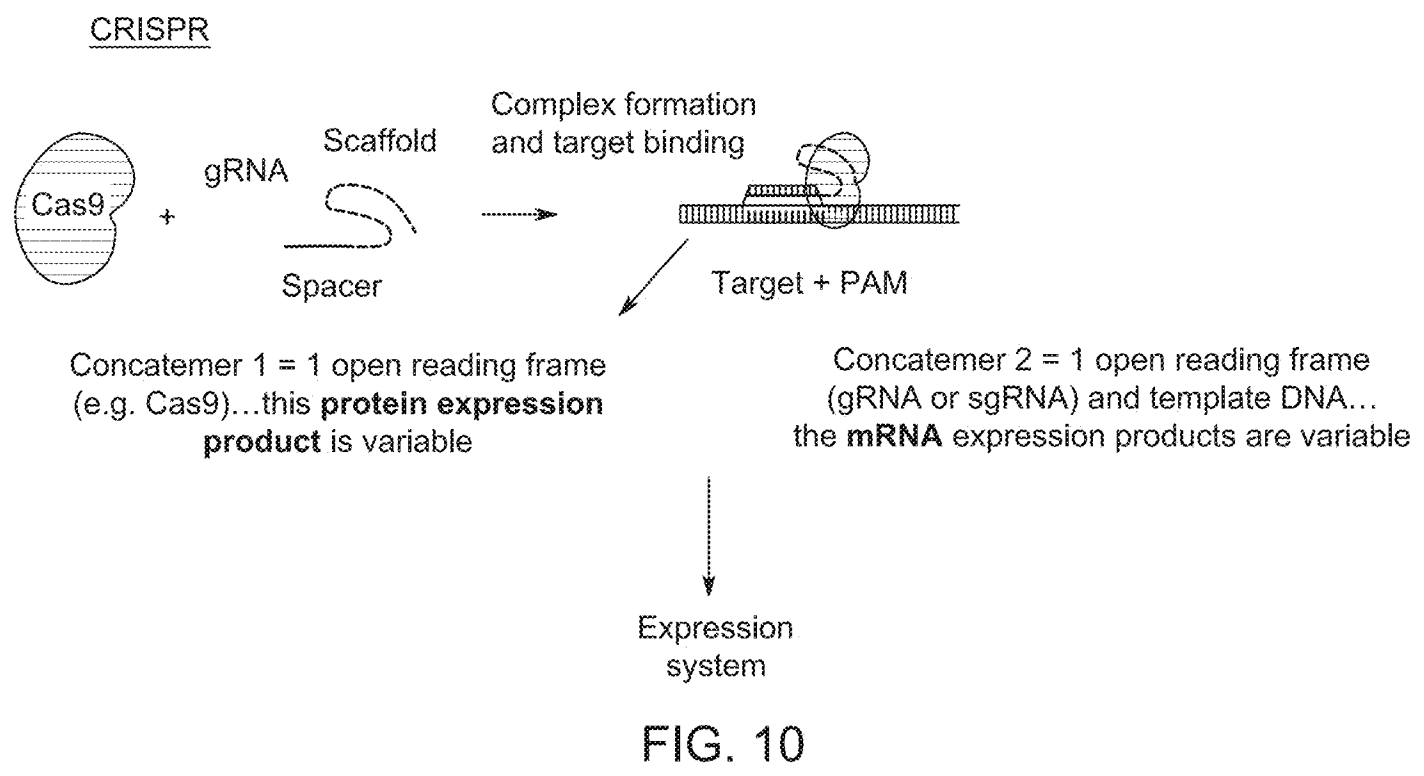

Cas9 +

Scaffold

Spacer

Complex formation
and target binding

Target + PAM

Concatemer 1 = 1 open reading frame
(e.g. Cas9)…this **protein expression
product** is variable Concatemer 2 = 1 open reading frame
(gRNA or sgRNA) and template DNA…
the mRNA expression products are variable Expression
system

FIG. 10

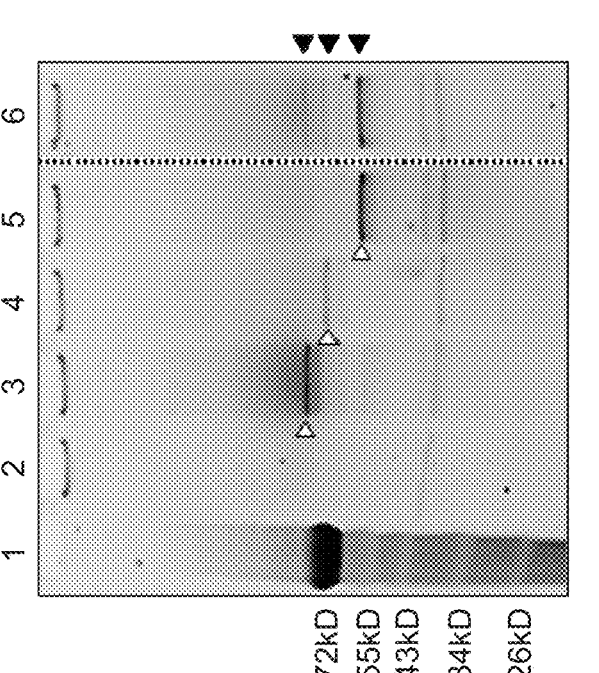
1 = Page ruler prestained ladder
2 = Express way, no template control (NTC)
3 = Express way + 500ng RCA_VP-1
4 = Express way + 500ng RCA_VP-2
5 = Express way + 500ng RCA_VP-3
6 = Express way + 40ng RCA_VP-1 + 40ng RCA_VP-2 + 422ng RCA_VP-3
FIG. 11

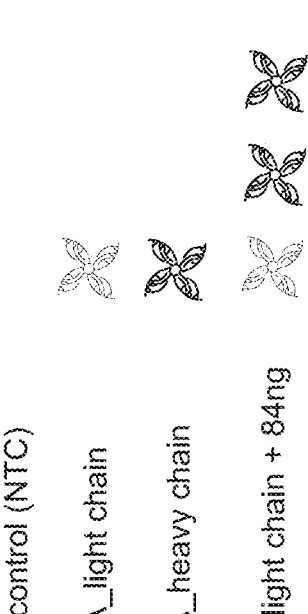
1 = Page ruler prestained ladder
2 = 1-Step, no template control (NTC)
3 = 1-Step + 125ng RCA_light chain
4 = 1-Step + 125ng RCA_heavy chain
5 = 1-Step + 42ng RCA_light chain + 84ng RCA_heavy chain
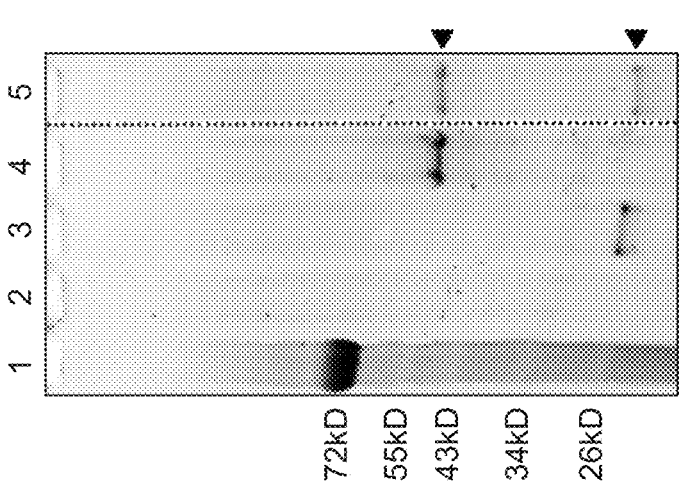
FIG. 12

EXPRESSION OF PRODUCTS FROM NUCLEIC ACID CONCATEMERS

SEQUENCE LISTING

The instant application contains a Sequence Listing which has been submitted electronically in ASCII format and is hereby incorporated by reference in its entirety. Said ASCII copy, created on May 15, 2019, is named 324586-1_SL.txt and is 13,566 bytes in size.

TECHNICAL FIELD

The disclosure generally relates to expression of recombinant products from nucleic acid concatemers, and, in certain embodiments, relates to a ratiometric co-expression of recombinant products from nucleic acid concatemers. The ratiometric co-expression has been demonstrated in both in vivo and cell free expression systems.

BACKGROUND

Recombinant products, including proteins, antibodies, and nucleic acids, have been widely used in clinical applications. Such recombinant products may harness nucleic acid and/or protein expression machinery to generate products of interest with clinical utility. For example, immunotherapy and other cell therapies frequently utilize viral vectors to deliver a genetic payload to treat a specific disease target. In one example, a viral vector delivery of a payload for genetic modification of cells with the chimeric antigen receptor for CAR-T immunotherapy may be used for treating certain types of blood cancer. Other applications for viral vectors include uses in cancer vaccines, monogenic disease and infectious disease.

Recombinant DNA technology has been used in production of recombinant products. However, certain desired products may involve multiple components that are complexed or that otherwise operate together. Production of such multi-component expression products may be complex. One common approach of producing recombinant products may involve separating different components into multiple plasmids. For example, co-expression of multiple plasmid constructs may be performed in both in vivo and in vitro settings. In some examples, multiple plasmid constructs may be transiently transfected into cultured cells, and those cultured cell are used produce desired recombinant products such as viral vectors, proteins, etc.

However, certain challenges are associated with using multiple plasmid constructs in cells. One of the challenges is the ratiometric control of co-expression of multiple plasmid constructs. For example, it has been reported that when each plasmid construct encodes a separate protein, a co-expression of the two (or more) proteins from the corresponding plasmids in a transfection procedure inside single cells may result in proteins being expressed at widely varying ratios, with a subpopulation of cells only expressing one of the desired proteins.

Several approaches have been attempted to improve the control of ratiometric co-expression of proteins and to achieve a desired ratio of proteins in single living cells. For example, instead of using two or more separate plasmids, a multi-cistronic plasmid may be constructed. For example, a single dual promotor plasmid with an internal ribosome entry site (IRES) and a viral 2A peptide can be used to drive co-expression of two or more proteins with reduced heterogeneity, although this requires the expense of laboriously cloning each open reading frame into the multi-cistronic plasmid and consequently increasing the size of the plasmid construct. In addition, since plasmids contain additional sequences necessary for maintenance in bacteria, the use of plasmids requires post-production purifications and QC analytics to prove absence of bacterial contaminants in the plasmid production, which posts a significant challenge for cGMP (clinical good manufacturing) process. The latter is especially challenging as the size of the plasmid construct increases and becomes difficult to distinguish from bacterial chromosomal DNA, which complicates post-production purification of plasmid DNA.

Therefore, a need still exists for systems and methods for reliably controlled expression of recombinant products in both in vitro and in vivo expression systems, especially with minimal labor for preparation.

BRIEF DESCRIPTION

A summary of certain embodiments disclosed herein is set forth below. It should be understood that these aspects are presented merely to provide the reader with a brief summary of these certain embodiments and that these aspects are not intended to limit the scope of this disclosure. Indeed, this disclosure may encompass a variety of aspects that may not be set forth below.

In one embodiment, a method is provided that includes the steps of formulating a concatemer mixture comprising at least a first nucleic acid concatemer and a second nucleic acid concatemer having a predefined ratio to one another, wherein the first nucleic acid concatemer comprises tandem repeats of a first nucleic acid sequence and wherein the second nucleic acid concatemer comprises tandem repeats of a second nucleic acid sequence; and co-expressing the concatemer mixture to generate a first expression product from the first nucleic acid sequence and a second expression product from the second nucleic acid sequence.

In another embodiment, a method is provided that includes the steps of formulating a mixture comprising at least two nucleic acid concatemers in a predefined ratio, wherein each of the nucleic acid concatemers comprises tandem repeats of two or more nucleic acid sequences; and the mixture is co-expressed to generate two or more expression products from each nucleic acid concatemer in the mixture.

In another embodiment, a method is provided that includes the steps of amplifying at least one template comprising a first nucleic acid sequence using strand-displacement rolling circle amplification to a generate a first concatemer comprising tandem repeats of the first nucleic acid sequence; contacting the first concatemer with a second concatemer comprising tandem repeats of a second nucleic acid sequence to form a concatemer mixture having a predefined ratio of the first nucleic acid concatemer to the second nucleic acid concatemer; co-expressing the concatemer mixture to generate a first expression product from the first nucleic acid sequence and a second expression product from the second nucleic acid sequence, wherein a ratio of the first expression product to the second expression product is proportional to the predefined ratio of the first nucleic acid concatemer to the second nucleic acid concatemer in the concatemer mixture.

In another embodiment, a method is provided that includes the steps of formulating a mixture comprising at least one nucleic acid concatemer and at least one plasmid having a predefined ratio to one another, wherein the at least one nucleic acid concatemer comprises tandem repeats of a first nucleic acid sequence and wherein the at least one plasmid comprises a second nucleic acid sequence; and co-expressing the mixture to generate a first expression product from the first nucleic acid sequence and a second expression product from the second nucleic acid sequence.

In another embodiment, a transfected cell is first provided and is transiently transfected with a nucleic acid concatemer comprising tandem repeats of a nucleic acid sequence and expressing at least one open reading frame in the nucleic acid sequence that encodes an expression product in the transfected cell. In one embodiment, the transfected cell that is provided has already been transfected with one or more nucleic acid concatemers and/or one or more plasmids. In this manner, the cell may be sequentially transfected with nucleic acid concatemers. In an alternative embodiment, the transfected cell stably expresses one or more desired products prior to transfection with a nucleic acid concatemer.

BRIEF DESCRIPTION OF THE DRAWINGS

These and other features, aspects, and advantages of the present disclosure will become better understood when the following detailed description is read with reference to the accompanying drawings in which like characters represent like parts throughout the drawings, wherein:

FIG. 9 is a schematic illustration of an embodiment of adeno-associated virus vector product expression according to embodiments of the disclosure;

FIG. 10 is a schematic illustration of an embodiment of CRISPR product expression according to embodiments of the disclosure;

FIG. 11 is an agarose gel photograph showing stoichiometric expression of Adeno-associated virus (AAV) capsid proteins, according to embodiments of the present disclosure;

FIG. 12 is an agarose gel photograph showing stoichiometric expression of light and heavy chain polypeptides, according to embodiments of the present disclosure;

DETAILED DESCRIPTION

Figure 1:
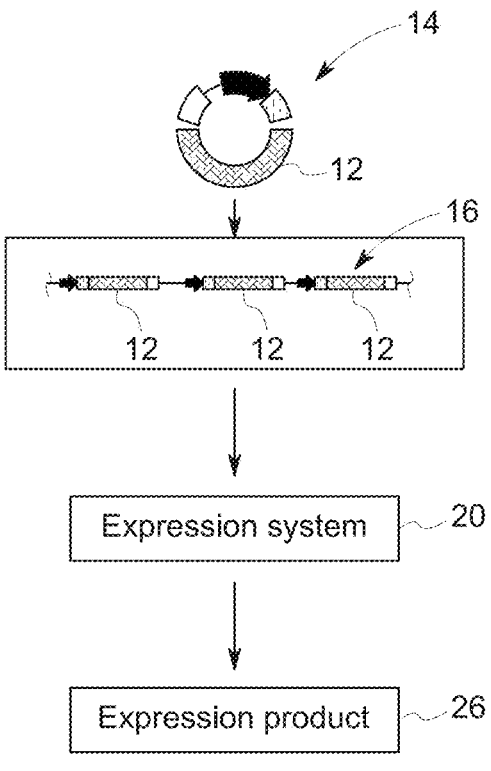
FIG. 1 is a schematic illustration of a generation of a concatemer for use in an expression system to generate a desired expression product according to embodiments of the disclosure.

One or more specific embodiments will be described below. In an effort to provide a concise description of these embodiments, not all features of an actual implementation are described in the specification. It should be appreciated that in the development of any such actual implementation, as in any engineering or design project, numerous implementation-specific decisions must be made to achieve the developers' specific goals, such as compliance with system-related and business-related constraints, which may vary from one implementation to another. Moreover, it should be appreciated that such a development effort might be complex and time consuming, but would nevertheless be a routine undertaking of design, fabrication, and manufacture for those of ordinary skill having the benefit of this disclosure.

Expression of products from nucleic acids that are a large size (i.e. high molecular weight) has been associated with low efficiency. Such low efficiencies may be the result of poor transfection efficiency of the larger nucleic acids, in turn leading to decreased generation of the desired end product, as well as DNA sequence-based competition between nucleic acids for host factors required for transcription and translation. It has been previously shown that transfection efficiency decreases as a function of DNA size, and plasmids greater than 10 kb in size have been shown to have dramatically decreased transfection efficiencies compared to plasmids of smaller sizes. Provided herein are expression techniques that use DNA concatemers or DNA concatemer mixtures, whereby the concatemer includes tandem repeats of a nucleic acid sequence coding for a desired expression product, such as a protein or nucleic acid expression product. In certain embodiments, the disclosed concatemer may be larger (e.g., at least 10 kb) than sizes previously associated with poor efficiency. However, as disclosed herein, two or more concatemers nonetheless achieve high transfection efficiency when mixed together, despite their large size. Also, one or more concatemer(s) mixed with a plasmid of smaller size also achieves high transfection efficiency, despite the large size of one of the two. In one embodiment, the concatemer is generated using strand-displacement amplification, such as rolling circle amplification (RCA), to create a plurality of concatemers of varying sizes and comprise tandem repeats of the nucleic acid sequences coding for the desired expression products. That is, the number of tandem repeats in each individual concatemer nucleic acid molecule may be unknown. Nonetheless, high transfection efficiencies and generation of desired expression products may be achieved even in the context of variable and/or mixed concatemer sizes that are the result of RCA. Further, the robust production and desired ratiometric control of desired co-expression products may be achieved even without knowing an exact number of tandem repeats as provided herein, and without controlling for sequenced-based competition between nucleic acid sequences for host factors.

Further, as disclosed herein, the DNA concatemers may be used in conjunction with co-expression systems to predictably co-express two or more expression products in a ratiometric manner. Two or more concatemers may be transfected and co-expressed to generate a co-expression product. The ratiometric expression may occur using concatemers with unknown numbers of tandem repeats of expression sequences for the desired end product. In certain embodiments, at least one of the concatemers has a size greater than about 10 kb. The transfection and co-expression of the two or more concatemers may occur in a single cell or a cell-free expression system. This is an unexpected result due to the conventional wisdom regarding the relationship between size and transfection efficiency. This is also unexpected due to the unpredictable nature of DNA sequence-based competition for host factors that regulate transcription and translation. For example, due to the large size of nucleic acid concatemers (e.g. a typical nucleic acid concatemer may have a size greater than 10 kb), the conventional wisdom is that a DNA cocktail comprising two or more different nucleic acid concatemers is not expected to efficiently enter a single cell and is not expected to generate the desired expression products, especially when the nucleic acid concatemers are unprocessed (for example, the nucleic acid concatemers are without further processing after generation). In addition, sizes of the concatemers typically cannot be accurately determined, and also are not uniform in size, making the design of such a cocktail or mixture (comprising two or more concatemers mixed at a predetermined or defined ratio) even more challenging.

As disclosed herein, a nucleic acid concatemer mixture comprising a first and a second concatemers and formulated using a defined ratio may be used to co-express the concatemer mixture to generate a co-expression product that includes at least a first and a second expression product, resulting from the first nucleic acid concatemer and the second nucleic acid concatemer of the concatemer mixture, respectively. In certain embodiments, the ratio of the first and the second expression products is proportional to the defined ratio of the first and the second nucleic acid concatemer in the concatemer mixture.

The use of concatemers generated by RCA to express desired end products provides benefits over other expression templates, such as plasmid constructs. Rolling circle amplification enables rapid production of specific DNA sequences (e.g. DNA minicircles) that are entirely relevant and bioactive for the intended application, for example that encode a minimal viral vector comprising packaging, transduction and expression elements and proteins required for virus production. This allows for increased specific activity of the DNA (coding sections per mass of DNA). In contrast, plasmids contain additional sequences necessary for maintenance in bacteria but unnecessary for the intended application. Because RCA concatemers are not manufactured in bacteria, the use of RCA avoids potential contamination of the final DNA product with extraneous bacterial components or purification reagents. The disclosed concatemer synthesis is performed without bacteria and therefore is bacterially-derived endotoxin-free. RCA concatemers also eliminate or reduce the need for large-scale bacterial growth, DNA purification columns, endotoxin removal and quality control associated with bacterial-derived products, such as QC analytics to prove absence of bacterial contaminants (genomic DNA and RNA) in the plasmid product. In contrast, nucleic acid concatemers can be prepared and propagated without bacteria and therefore, require minimal post-production purification, thus providing cost and complexity benefits adapted for cGMP manufacturing. Further, RCA-generated concatemers may be used to encode products that are toxic to bacteria, which are difficult to scale up in a bacteria-based system. This is because constructs that may be used to encode for products that are toxic are difficult to maintain due to leaky expression of the product during bacterial growth, leading to loss of the construct from the bacteria or death of the bacteria.

Furthermore, RCA-generated concatemers can enable simplified point-of-need DNA production and scale-up. Milligram to gram quantities of rolling circle amplified DNA can be produced inexpensively from template DNA in less than a day using an isothermal amplification reaction. The total "hands-on" time to produce 5 mg of RCA DNA is less than one hour. In contrast, supercoiled plasmid isolated from a DH5alpha strain of E. coli using an endotoxin-free purification columns requires roughly eight hours. Thus, rolling circle amplification is expected to provide a simpler and less expensive manufacturing process compared with standard bacterial-derived plasmids.

Still further, the RCA process permits insertion of modified nucleotides into amplified DNA, a possibility that is limited in plasmid-based systems in living cells. Modified nucleotides may contribute to creating functionalized DNA with enhanced nuclease resistance, enhanced stability, prolonged gene expression, and increased genomic integration efficiency. In one embodiment, transfection of RCA DNA modified with phosphorothioated nucleotides provided prolonged protein expression compared with RCA DNA containing only standard nucleotides. Accordingly, in one embodiment, the present techniques may be used to produce or manufacture expression products from concatemers with incorporated modified nucleotides.

FIG. 1 is a schematic illustration of production of a desired expression product using at least one concatemer as provided herein. An expression sequence 12 in a circular template 14 is used to generate a concatemer 16 including tandem repeats of the expression sequence 12 using rolling circle amplification (RCA). The concatemer 16, once generated, may be purified or otherwise cleaned before being used in an expression system 20 that, in operation, acts on the concatemer 16 to express the expression sequence 12 to generate an expression product 26. However, in certain embodiments, the concatemer 16 may be applied without addition processing in the expression system 20. The expression system 20 may be a cell-based or cell-free expression system as disclosed herein. Once generated, the expression product 26 may be collected for use in an appropriate treatment protocol or other application. The expression product 26 of the concatemer 16 may include one or more proteins and/or nucleic acid expression products.

In certain embodiments, the concatemer 16 may be used alone or in conjunction with other concatemers 16 in the expression system 20 (e.g., two or more concatemers 16) or with other expression vectors, such as in a mixture with plasmids that may be used in a cell-free expression system or co-transfected in a cell-based system to co-express multiple expression products 26. In a specific embodiment, a concatemer 16 of about 10 kb or greater in size may be used in a cell-based expression system to generate the expression product 26. In contrast to other techniques, the present disclosure demonstrates that concatemer and concatemer mixtures of large sizes are not subject to the same decrease in transfection efficiency in a cell-based expression system relative to plasmids of similar size, nor subject to DNA sequence-based competition for host factors that reduce the efficiency of co-expression in expression systems.

Figure 2:
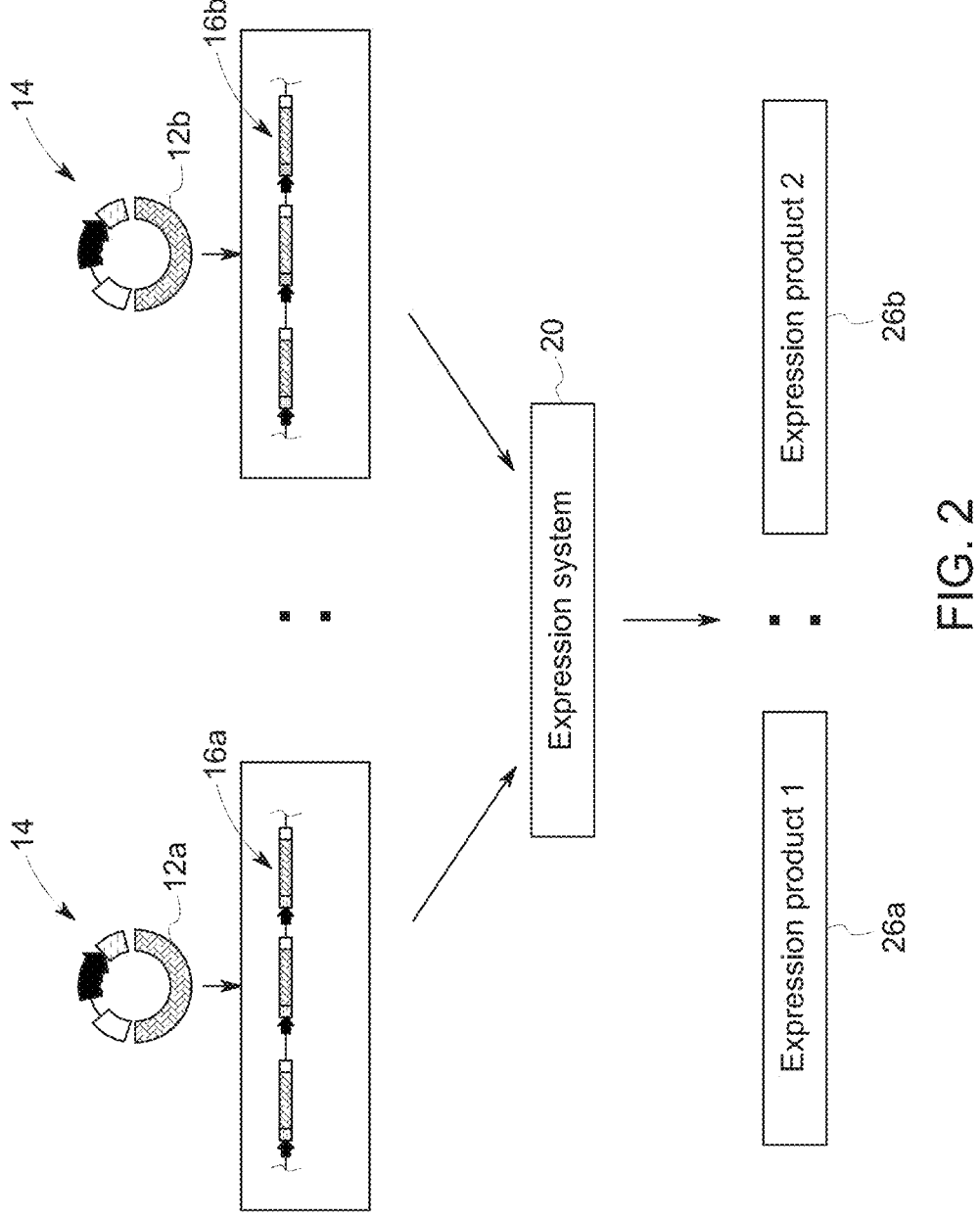
FIG. 2 is a schematic illustration of a generation of two or more concatemers for use in a co-expression system to generate a desired expression product or products according to embodiments of the disclosure.

FIG. 2 is a schematic illustration of co-expression of a of desired expression products using a mixture of a plurality of concatemers. A first concatemer 16a bearing tandem repeats of an expression sequence 12a and generated from a template 14a via RCA may be mixed with a second concatemer 12b bearing tandem repeats of an expression sequence 12b and generated from a template 14b via RCA as provided herein. The expression sequences 12a, 12b may be different such that the expression system 20 produces multiple expression products 26a, 26b. That is, rather than generating the different expression products 26a, 26b in different expression systems 20, the different expression products 26a, 26b may be co-expressed in the same expression system 20, e.g., produced at the same time. Further, the ratio of the expression products 26a, 26b (and so on) may be based on or proportional to the ratio of the concatemers 16a, 16b (and so on) in the mixture.

While the sizes of recombinant plasmids may be readily determined based on the sizes of the size of the plasmid construct together with any inserted expression sequence, sizes of concatemers may vary. However, an embodiment of the present techniques involves assuming that each concatemer 16 is a monomer rather than attempting to determine an exact number of tandem repeats of the expression sequence 12 in each concatemer 16. This assumption is used in determining the molar ratio of the concatemers 16 to one another. For example, a first concatemer 16a may have tandem repeats of expression sequence 12a of a known base length of 1000 and a second concatemer 16b may have tandem repeats of expression sequence 12b of a known base length of 1500. Accordingly, to achieve a molar ratio of the first concatemer 12a:second concatemer 12b of 1:1, the total weight of the second concatemer 16b should be 1.5× that of the first concatemer 16a in a concatemer mixture used for co-expression. It should be understood that the concatemers 16 may both be single-stranded or both be double-stranded or a mixture of single and double stranded. For any additional concatemers 16, the molar ratio may also be determined. Table 1 summarizes an example of a molar ratio used for a three concatemer 16 co-expression system of adeno-associated virus (AAV) and using the assumption that the molar ratio may be based on monomers of the expression sequence 12 size (or a plasmid/circular construct bearing the expression sequence, such as the template 14).

TABLE 1

| Mass and molar ratios for AAV co-expression | | | | |
|---|---|---|---|---|
| Plasmid construct used as concatemer monomer size assumption | Size (kb) | Desired ratio | Micrograms DNA for molar ratio | Micrograms DNA for mass ratio |
| pscAAV-GFP | 4.4 | 1 | 1.00 | 1.00 |
| pAAV-RC6 | 7.3 | 1 | 1.66 | 1.00 |
| pHelper | 11.6 | 1 | 2.6 | 1.00 |

The molar ratio may be estimated based on the estimated sizes of the concatemers 12a, 12b and an estimated concentration of the concatemers 12a, 12b generated by RCA.

Accordingly, while co-expression of two or more proteins by transfecting separate plasmids in a single cell has been reported to occur with widely varying ratios of the expressed proteins (e.g., many subpopulations of cells only express one of the two protein constructs), the present techniques facilitate programmable ratios of co-expressed products that are proportional to a ratio of concatemers 16 used in the expression system 20. While concatemers carry uncertainties related to varying size, the present disclosure demonstrates that, nonetheless, using concatemers 16 to co-express desired expression products 26 yields robust expression in programmable ratios.

It should be understood that, in a co-expression workflow, the concatemers 16 may be mixed or formulated with predetermined or predefined ratios based on a desired ratio of the respective expression products 26. That is, to achieve a desired ratio of a first expression product 26a to a second expression product 26b, the concatemer mixture provided to the expression system 20 may be formulated with the concatemers 16a, 16b being present in the mixture at a predefined ratio to one another. For two concatemers 16, the ratio of concatemers 16 may be 1:1, 1:1.5, 1:2, 1:2.5, 1:3, 1:4, 1:5, 1:6, 1:7, 1:8, 1:9, 1:10, and so on. For three or more concatemers 16, the ratio of concatemers 16 may be expressed as $C_1:C_2:C_N$ where each of $C_1$, $C_2$, through $C_N$ may be 1, 1.5, 2, 2.5, 3, 4, 5, 6, 7, 8, 9, 10, and so on, and may not be the same integer. In certain embodiments, the ratio is a molar ratio rather than a simple mass ratio. In one embodiment, a molar ratio of concatemers 16 that is about 1:1 yields a ratio of respective expression products 26 that is about 1:1. Further, for co-expression systems comprising one or more DNA concatemers 16, the precise length of the DNA may be measured, rather than inferring or estimating concatemer size, to determine the appropriate ratio as disclosed.

In certain embodiments, a co-expression product may be formed by formulating a concatemer mixture comprising a first nucleic acid concatemer and a second nucleic acid concatemer at a defined ratio; co-expressing the concatemer mixture to generate at least a first expression product and a second expression product each resulting from the first nucleic acid concatemer and the second nucleic acid concatemer of the concatemer mixture, respectively; where a ratio of the first expression product and the second expression product is proportional to the defined ratio of the first nucleic acid concatemer and the second nucleic acid concatemer in the concatemer mixture. In certain embodiments, the ratio of the first and the second expression products and the defined ratio of the first and second nucleic acid concatemers are substantially the same.

Figure 3:
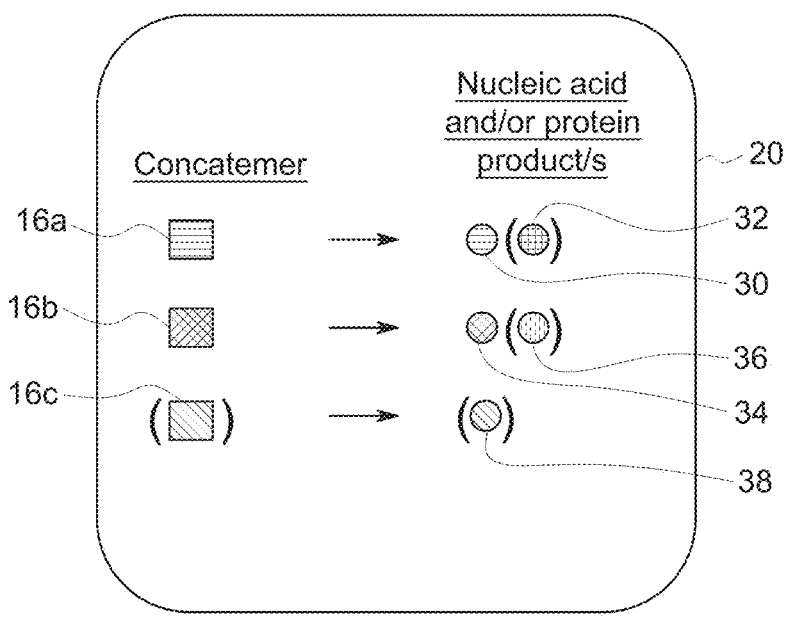
FIG. 3 is a schematic illustration of potential end products of a co-expression system according to embodiments of the disclosure.
Figure 4:
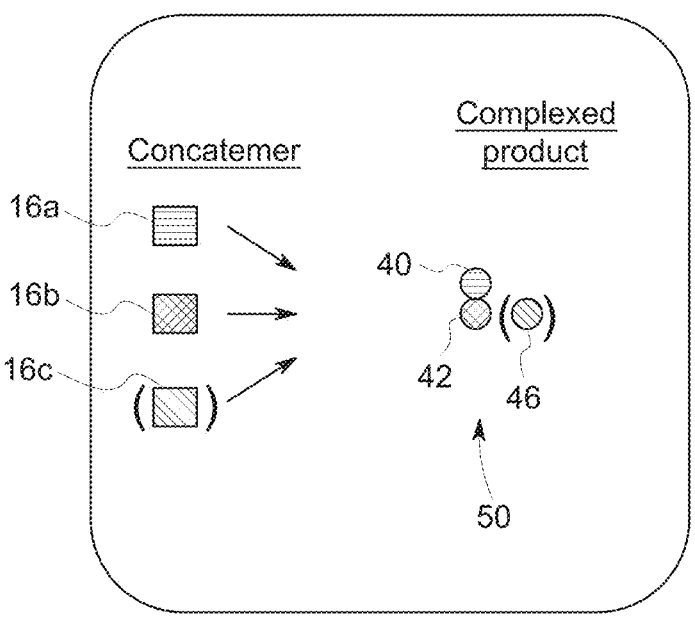
FIG. 4 is a schematic illustration of potential complexed end products of a co-expression system according to embodiments of the disclosure.
Figure 5:
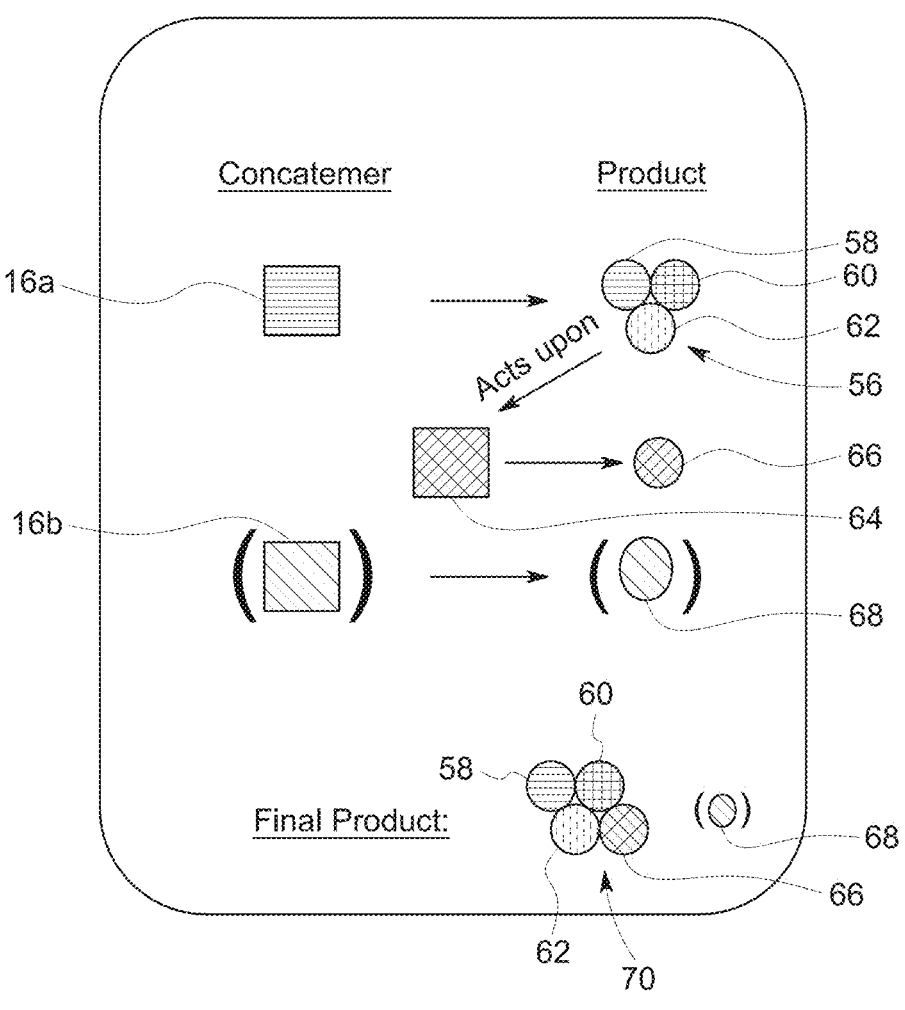
FIG. 5 is a schematic illustration of potential end products that act on one another or on another nucleic acid or protein of a co-expression system according to embodiments of the disclosure.

FIGS. 3-5 are schematic illustrations of embodiments of co-expression of nucleic acid concatemers to form desired end products. The co-expression product or products may be in a form of a non-complexed co-expression product or a complexed co-expression product. In certain embodiments, the non-complexed co-expression product may comprise two or more expression products that are co-expressed and exist in a non-complexed form. For example, the co-expression product may comprise a first expression product 30 and a second expression product 34 that are co-expressed and do not subsequently form a complex with each other, as shown in FIG. 3. Each of the expression products may be independently a protein, a RNA, or a combination thereof. In addition, each concatemer 16 (16a, 16b, optionally 16c) may produce multiple expression products, shown as expression products 32, 36, 38.

In certain embodiments, a complexed co-expression product may comprise two or more expression products 40, 42 that are co-expressed from respective concatemers 16a, 16b and subsequently form a complex 50 with each other, as shown in FIG. 4. For example, the complexed co-expression product may comprise a first expression product 40 and a second expression product 42 that are co-expressed and form the complex 50 with each other. Each of the expression products may be independently a protein, a RNA, or a combination thereof. In addition, as shown, other concatemers 16c may also generate expression products (e.g., expression product 46) that may also form part of the complex 50. Non-limiting examples of complexed co-expression products may include antibodies (e.g. monoclonal antibody (mAb)), virus-like particles, CRISPR, or lentivirus.

FIG. 5 is an embodiment in which the co-expression product may comprise a first expression product that acts upon a molecule. The first expression product may be a complexed co-expression product 56 formed from separate expression products 58, 60, 62. In one embodiment, the first expression product 56 may be an enzyme and the acted-upon molecule 64 may be a substrate that the enzyme acts upon. In one embodiment, the molecule 64 is a concatemer. In one embodiment, the interaction of the complex 56 with the molecule yields a product 66, which in turn may form a complex 70 with the complex 56 and its components. In another embodiment, the first expression product may be a protein and the second expression product may be a DNA. The expression system may also include additional concatemer/s (e.g., concatemer 16b) that form expression products (e.g., expression product 68) that are not part of the end complex 70. Non-limiting examples of co-expression products that act upon a molecule, wherein the molecule is a concatemer, include recombinant adeno-associated virus (AAV) production from DNA transfected cells.

In accordance with the current disclosure, a concatemer mixture comprising a first nucleic acid concatemer and a second nucleic acid concatemer at a defined ratio is formulated. The concatemer mixture is co-expressed to generate at least a first expression product and a second expression product each resulting from the first nucleic acid concatemer and the second nucleic acid concatemer of the concatemer mixture, respectively, where a ratio of the first expression product and the second expression product is proportional to the defined ratio of the first nucleic acid concatemer and the second nucleic acid concatemer in the concatemer mixture.

In certain embodiments, at least one of the first and the second nucleic acid concatemers comprises a minimalistic expression sequence. The minimalistic expression sequence encodes the desired product or products with no extraneous sequences that are required for DNA propagation in a host cell. The minimalistic expression sequences may be designed in silico and synthesized in vitro. In one embodiment, each respective expression sequence 12 may comprise an open reading frame (ORF) and a promotor operably linked to the open reading frame. In certain embodiments, at least one of the expression sequences may comprise one promoter operably linked to more than one ORFs. For example, one of the expression sequences may include a promoter functionally linked to two different ORFs.

In embodiments in which two or more concatemers 16 are used, a concatemer mixture provided herein may include a mixture of the two or more concatemers 16, with each respective concatemer 16 having different expression sequences 12 (i.e., nucleic acids having different sequences) relative to one another. It should be understood that the concatemer mixture may be formed from a first subset of a plurality of concatemers 16 of a first type (having tandem repeats of a first nucleic acid sequence) and a second subset of a plurality of concatemers 16 of a second type (having tandem repeats of a second nucleic acid sequence that is different from the first nucleic acid sequence) such that the mixture comprises concatemers 16 of the first subset and the second subset. Further, the concatemer mixture may, in embodiments, comprise a third subset of concatemers 16 of a third type (having tandem repeats of a third nucleic acid sequence that is different from the first nucleic acid sequence and the second nucleic acid sequence) and so on. As noted, within each individual subset, the size (base length) of the concatemers 16 and their corresponding tandem repeat numbers may vary.

Figure 6:
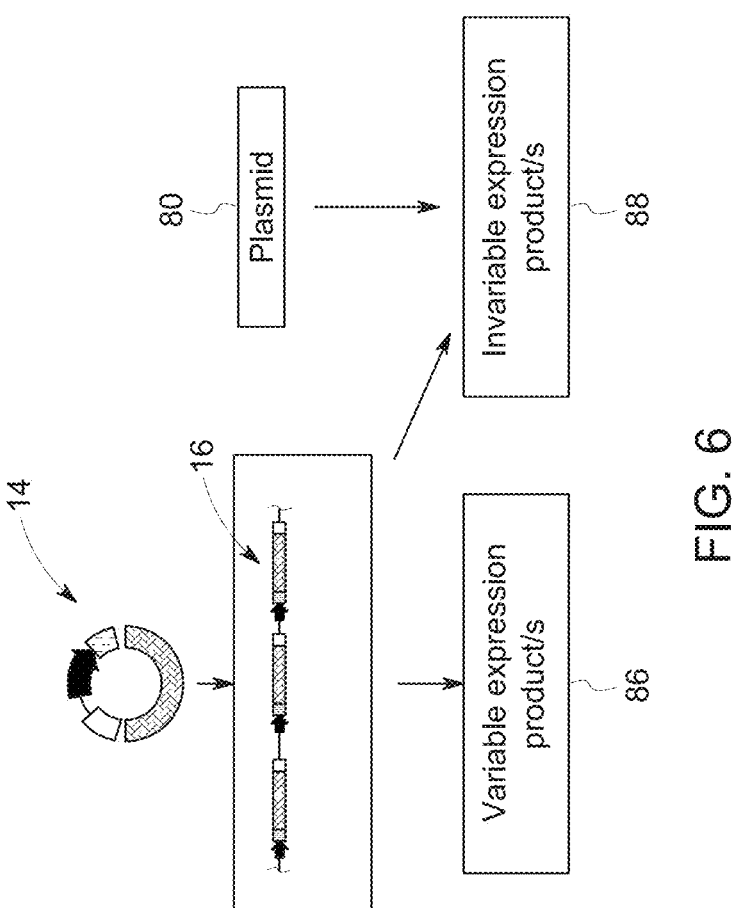
FIG. 6 is a schematic illustration of a mixed expression strategy in which all or some of the desired expression products of a multi-product system are expressed using concatemers according to embodiments of the disclosure.

FIG. 6 is a schematic illustration of different implementations of techniques for generating expression products in accordance with embodiments of the present disclosure. In some embodiments, it may be desirable to generate multiple expression products to form a complex or that interact with one another to form a final desired end product. During an expression workflow, these expression products may be divided into different expression vehicles (different concatemers 16 or, in some embodiments a mix of one or more concatemers 16 and one or more plasmids, such as a plasmid 80 or a plasmid 82) depending on the type of expression product or the desired customization or variability of the expression product.

For example, certain types of expression products may include customizable nucleic acid expression products 86. The customizable nucleic acid expression products 86 may be generated by using a template 14 with a customized or desired expression sequence. It may be hard to predict which particular nucleic acid expression product 86 may be of interest to the end user. Accordingly, rather than incorporate the nucleic acid sequence for a variable nucleic acid expression product 86 into an expression sequence 12 that includes other desired end products that are more constant or invariable, a kit or expression product production system 87 as provided herein may separate the customizable or more variable regions into a separate template 14 and concatemer 16. In this manner, the more invariable expression products 88 may be provided as separate templates 14 that are pre-made or part of a kit assembly that incorporates the expression sequence 12 for the customizable expression products 86 into separate concatemers 16 or plasmids 82. In another embodiment, plasmids may be selected for more constant or predictable components that do not change from application to application while DNA concatemers (amplified from plasmid or minicircle templates) may be selected for components that are variable or customizable across applications. Examples of such separate constructs are discussed below with regard to FIGS. 7-10.

Lentivirus

Figure 7:
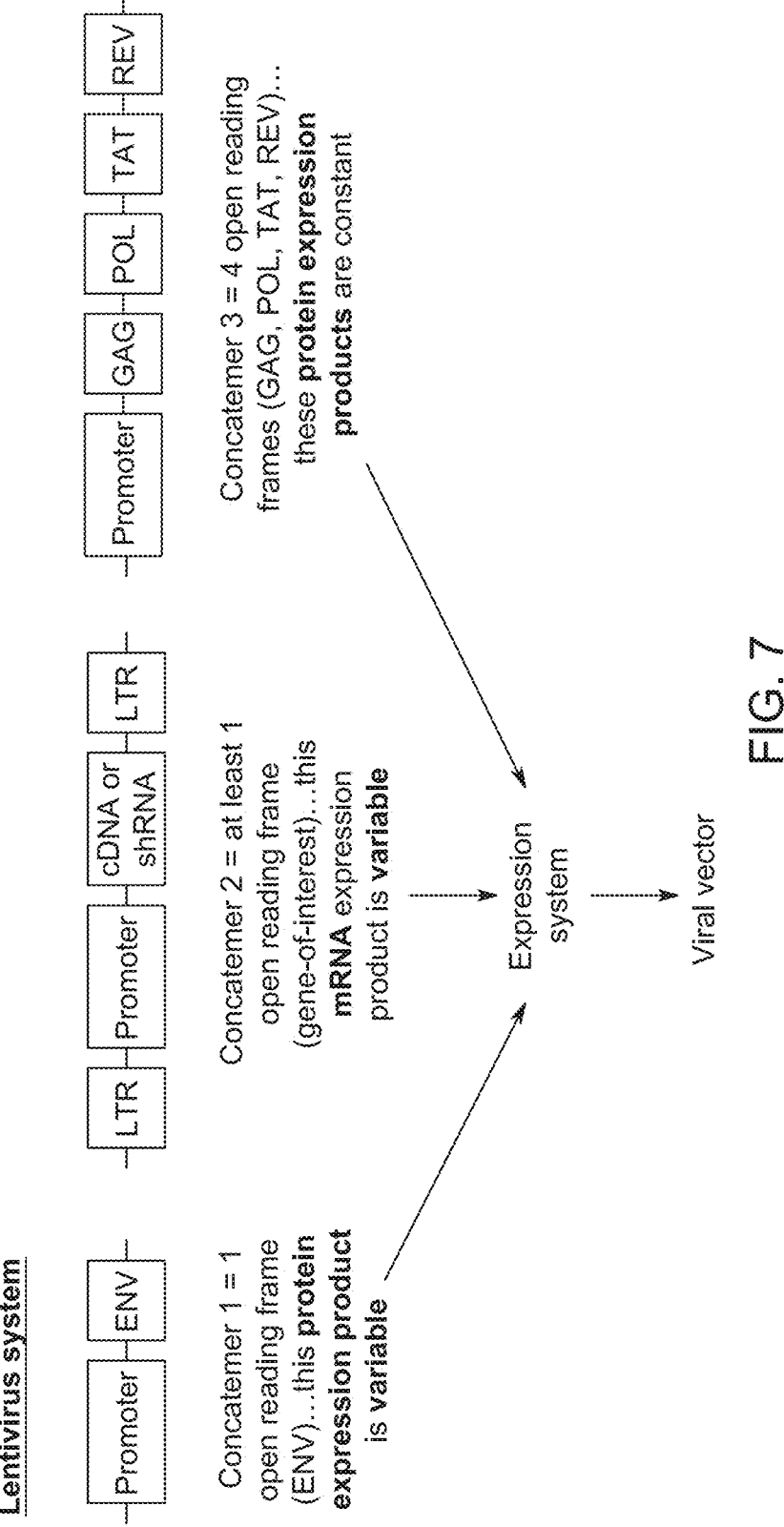
FIG. 7 is a schematic illustration of an embodiment of lentivirus vector product expression according to embodiments of the disclosure.
Figure 8:
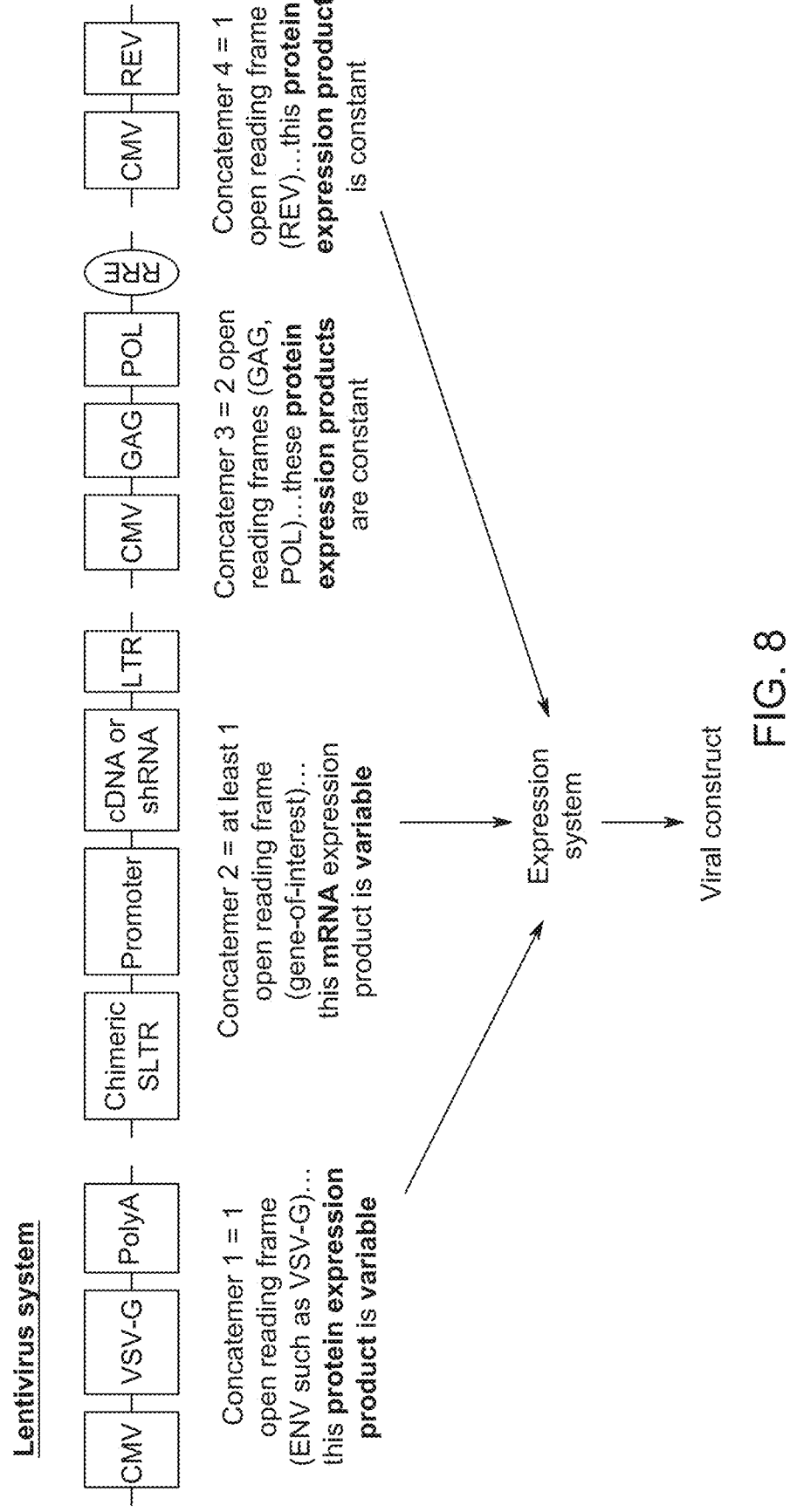
FIG. 8 is a schematic illustration of an embodiment of lentivirus vector product expression according to embodiments of the disclosure.

FIGS. 7-8 are schematic illustrations of a lentivirus viral vector production system. Production of lentivirus viral vectors may be useful for a variety of gene therapy applications, including during production of CAR-T therapy. In particular, lentivirus vectors as produced using the techniques disclosed herein may be used in the production of CAR-T therapy cells. In one embodiment, a lentivirus transgene of a lentivirus vector produced by the disclosed techniques may code for a chimeric antigen receptor.

Lentivirus has a linear single-stranded RNA (ssRNA) genome. In the depicted embodiment for second-generation lentiviral vector production, the ENV protein (e.g., VSV-G) may be encoded by an expression sequence of a first concatemer, the desired transgene sequence flanked by long terminal repeat (LTR) sequences may be part of an expression sequence of a second concatemer, and packaging proteins may be present on a third concatemer with ORFs encoding the GAG, POL, REV, and TAT genes (FIG. 7). In another arrangement for third-generation lentivirus production (FIG. 8), the packaging proteins are divided further into two packaging concatemers, with GAG, POL being present on one concatemer and REV being present on the other concatemer.

In accordance with the current disclosure, efficient production of functional lentivirus was achieved by formulating and transfecting mixtures of RCA DNA (separately encoding VSV-G envelope, GAG/POL, REV, and a GFP mRNA) at stoichiometric ratios in HEK293T cells. Plasmids encoding GAG/POL (pLP1, Invitrogen), REV (pLP2, Invitrogen), VSV-G envelope (pLP/VSVG, Invitrogen), and a packaging GFP mRNA (pLenti-GFP, Cell Biolabs) were amplified by RCA to generate high molecular weight, hyper-branched concatemers comprising tandem repeats of each plasmid to evaluate successful viral vector production. The viral vector may be produced from living cells or through cell-free expression In accordance with the current disclosure, a concatemer mixture comprising a plurality of nucleic acid concatemers with a defined ratio between each of the plurality of nucleic acid concatemers is formulated. The concatemer mixture is co-expressed to generate a plurality of expression products each resulting from a respective nucleic acid concatemer, where a ratio between each of the plurality of expression products is proportional to the defined ratio between each respective nucleic acid concatemer in the concatemer mixture.

While the disclosed embodiments relate to a plurality of concatemers being used to generate the lentivirus vector, in other embodiments, a mix of concatemers and plasmids is also contemplated. In one embodiment, only the transgene is expressed using a concatemer while plasmid constructs encoding other components are co-transfected with the transgene concatemer in the co-expression system. In another embodiment, the desired transgene and ENV protein are co-expressed from a mixture of two different concatemers while plasmid encoding other components are co-transfected with the concatemer mixture into the co-expression system. The present techniques may include simultaneous transfection of one or more concatemers including the lentivirus transgene as well as any plasmids or concatemers with open reading frames for other components of the viral vector (one or more packaging concatemers or plasmids; and one envelope concatemer or plasmid) into an expression system, such as HEK293T producer cells or A293T cells. The co-expression may be performed in cells or cell free.

In certain embodiments, individual RCA products were mixed at a molar ratio of 1:1:1:1 and transfected into HEK239T cells. In certain embodiments, one or more RCA DNA concatemers may be replaced by plasmid DNA. Different ratios of RCA DNA to plasmid DNA may be used, for example, with 1:3:3:3 and 3:1:1:1 molar ratios of pLenti-GFP:LP1:LP2:LP3, respectively. In either case, concatemeric RCA DNA efficiently cooperated with plasmid DNA to generate comparable amounts of lentivirus.

Adeno-Associated Virus (AAV)

Wild-type AAV has a linear single-stranded DNA (ssDNA) genome of approximately 4.7-kilobases (kb), with two 145 nucleotide-long inverted terminal repeats (ITR) at the termini. The ITRs flank the two viral genes—Rep (replication) and Cap (capsid), encoding non-structural and structural proteins, respectively. The Rep gene encodes four regulatory proteins, Rep78, Rep68, Rep52 and Rep40. These proteins are involved in AAV genome replication. The Cap gene encodes three capsid proteins, VP1 (virion protein 1), VP2 and VP3. Among AAV serotypes, AAV2 is the most widely used for in vitro and in vivo gene delivery.

The AAV ITRs contain all cis-acting elements involved in genome rescue, replication and packaging, and are segregated from the trans-acting viral encoding regions, i.e., Rep and Cap gene regions. In a recombinant AAV (rAAV) vector design, cis-acting viral DNA elements (e.g. ITR) may be in linkage with sequences of interest, whereas the Rep and Cap gene regions may be provided in trans. Typically, rAAV particles are generated by transfecting producer cells with a plasmid (AAV cis-plasmid) containing a cloned recombinant AAV genome composed of DNA of interest flanked by the AAV ITRs, and a separate plasmid expressing in trans the viral Rep and Cap genes. The adenovirus helper factors, such as E1A, E1B, E2A, E4ORF6 and VA RNAs, may be provided by either adenovirus infection or transfecting into production cells a third plasmid that provides these adenovirus helper factors. If HEK293 cells are used as AAV production cells, the helper factors include E2A, E4ORF6 and VA RNAs since HEK293 cells already contain the E1A/E1b gene.

One technique for production of recombinant AAV, particularly recombinant AAV2, relies on wild-type adenovirus infection into the cell lines that harbor AAV Rep/Cap genes, as well as the AAV vector DNA. Another method, the helper-free method, is based on the adenovirus-free transient transfection of all elements that are required for AAV production in host cells such as HEK293 cells. It involves the co-transfection of AAV production cells with 3 plasmids: (1) an AAV transfer plasmid, where the gene of interest (e.g., "transgene") is placed between the two ITRs; (2) a plasmid that carries the AAV Rep-Cap genes; and (3) a helper plasmid that provides the helper genes isolated from adenovirus. These genes (E4, E2a and VA) mediate AAV replication. The transfer plasmid, Rep/Cap, and the helper plasmid are transfected into a host cell, for example, a HEK293 cell, which contains the E1A/E1b gene, to produce infectious AAV particles.

Although the method using wild-type adenovirus-inducible AAV producer cell lines can be scaled up in cultures and produce AAV vectors with very high titers, it is very challenging to completely eliminate the adenovirus from AAV product, and contamination of wild-type adenovirus is highly undesirable in terms of vector safety and specificity. On the other hand, although the transient-transfection method generates high-titer AAV vectors that are free of adenovirus, the process is very labor-intensive and expensive.

In addition, it has been reported that recombinant co-expression of AAV in a single cell from separate plasmids in a transfection procedure are expressed at widely varying ratios. The AAV cap gene encodes for three structural proteins (VP1, VP2, and VP3) in approximately 1:1:10 stoichiometry. To achieve this desirable stoichiometry, recombinant methods for generating AAV capsid protein generally utilize complicated promoter induction and/or combinations of low- and high-copy number plasmids to achieve 1:1:10 expression ratios of VP1, VP2, and VP3, such as in yeast-based expression.

In accordance with the current disclosure, a stoichiometric expression of VP1, VP2, and VP3 capsid proteins has been demonstrated using one or more concatemers. The expression may be performed in cells or cell-free. In certain embodiments, mixing and supplementing nucleic acid concatemers may be performed at a 1:1:10 ratio in cell-free protein expression reactions.

In accordance with the current disclosure, a concatemer mixture comprising a plurality of nucleic acid concatemers with a defined ratio between each of the plurality of nucleic acid concatemers is formulated. The concatemer mixture is co-expressed to generate a plurality of expression products each resulting from a respective nucleic acid concatemer, where a ratio between each of the plurality of expression products is proportional to the defined ratio between each respective nucleic acid concatemer in the concatemer mixture.

In certain embodiments, each of the plurality of nucleic acid concatemers separately encode critical replication and viral capsid factors in addition to the desired transgene. In certain embodiments, at least one of the nucleic acid concatemers comprises a minimalistic expression sequence. The minimalistic expression sequence may be designed in silico and synthesized in vitro (for example, SEQ ID #1-#3 listed below). In another embodiment, the transgene (e.g., the transgene payload) is present on a separate concatemer from the REP/CAP concatemer or concatemers. Further, another concatemer may include one or more helper sequences, depending on the desired expression system. While the disclosed embodiments relate to a plurality of concatemers being used to generate the AAV vector, in other embodiments, a mix of concatemers and plasmids is also contemplated. In one embodiment, only the transgene is expressed using a concatemer while plasmid constructs encoding other components are co-transfected with the transgene concatemer in the co-expression system. In another embodiment, the desired transgene and capsid proteins are co-expressed from a mixture of two different DNA concatemers while plasmid encoding other components are co-transfected with the concatemer mixture into the co-expression system. The present techniques may include simultaneous transfection of one or more concatemers including the AAV transgene as well as any plasmids or concatemers with open reading frames for other components of the viral vector.

CRISPR

FIG. 10 is a schematic illustration of a co-expression system to generate CRISPR/Cas9 genome editing is carried out with a Type II CRISPR system. When utilized for genome editing, this system includes Cas9, crRNA, tracrRNA along with an optional section of DNA repair template that is utilized in either non-homologous end joining (NHEJ) or homology directed repair (HDR).

CRISPR/Cas9 often employs a plasmid to transfect the target cells. The main components of the plasmid include crRNA, tracrRNA, sgRNA, Cas9 protein, and repair template. crRNA contains a guide RNA that locates the correct section of host DNA along with a region that binds to tracrRNA. tracrRNA binds to crRNA and forms an active complex. Single guide RNAs (sgRNA) are a combined RNA consisting of a tracrRNA and at least one crRNA. Multiple crRNAs and the tracrRNA can be packaged together to form a single-guide RNA (sgRNA). This sgRNA can be joined together with the Cas9 gene and made into a plasmid in order to be transfected into cells. Once these have been assembled into a plasmid and transfected into cells the Cas9 protein with the help of the crRNA finds the correct sequence in the host cell's DNA and, depending on the Cas9 variant, creates a single or double strand break in the DNA.

The present techniques may also be used to produce or manufacture targeted CRISPR/Cas9 systems using concatemers/s 16 to replace a conventional plasmid-based technique. The first and the second nucleic acid concatemers may comprise a first and a second expression sequence, respectively. One of the first and the second expression sequences comprises an open reading frame (ORF) encoding a protein of interest (e.g. Cas9) and a promotor operably linked to the open reading frame. The other of the expression sequences could comprise an open reading frame (ORF) encoding crRNA, tracrRNA, sgRNA, or repair template.

Antibodies

Immunoglobulins or antibodies comprise heavy and light chains in characteristic stoichiometries. For example, immunoglobulin G (IgG) comprises two identical heavy chains and two identical light chains held together by disulfide bonds. Conventional recombinant methods for producing immunoglobulins may require complicated design of single-vector expression cassettes containing DNA, RNA, or protein sequence elements (such as different promoters, internal ribosomal entry sites, post-translation cleavage sites, or polyadenylation signals of different strength) to achieve a desired expression ratio of antibody heavy and light chains, such as in CHO cells. The expression ratio of light-chain to heavy-chain polypeptides has been recognized as a critical parameter toward the recombinant yield of a desired antibody as well as limiting undesirable aggregates and fragments.

The present techniques may also be used to produce or manufacture antibodies in which the expression ratio of the light-chain to heavy-chain polypeptides is produced in a more streamlined and robust manner by using a predetermined ratio of a first and second nucleic acid concatemer to, in turn, yield a desired ratio of light-chain to heavy-chain polypeptides. In one embodiment, a first and second nucleic acid concatemer may comprise a first and a second expression sequence, respectively, with each expression sequence comprising an open reading frame (ORF) and a promotor operably linked to the open reading frame. In certain embodiments, the ORF of the first and the second expression sequence may each encode a heavy chain and a light chain of the antibody, respectively. In certain embodiments, one of the expression sequences may include one promoter operably linked to more than one ORFs. For example, one of the expression sequences may include a promoter functionally linked to two different ORFs, one ORF encoding a heavy chain, and the other ORF encoding a light chain of the antibody. In another embodiment, a concatemer mixture may be formulated to express bispecific antibodies, in which the first concatemer encodes a first expression sequence comprising light-chain and heavy-chain domains of a first antibody while the second concatemer encodes a second expression sequence comprising light-chain and heavy-chain domains of a second antibody.

Virus-Like Particles

The present techniques may also be used to produce or manufacture virus-like particles. Non-limiting examples of virus-like particles include HPV and Gardasil (Human Papillomavirus Quadrivalent Types 6, 11, 16, and 18) vaccine. HPV encodes two capsid proteins, L1 and L2. The major capsid protein, L1, may assemble spontaneously into a 72-pentamer icosahedral structure that closely resembles native virions. The minor capsid protein, L2, while not required for capsid formation, may be present at an average of about 36 molecules of L2 per capsid (estimated L1:L2 ratio of about 9:1 to 11:1). Gardasil (Human Papillomavirus Quadrivalent Types 6, 11, 16, and 18) vaccine is a recombinant VLP formulation of four different L1 capsomers, each individually expressed from baker's yeast.

The first and the second nucleic acid concatemers may comprise a first and a second expression sequence, respectively. The first and the second expression sequences may comprise open reading frame (ORF) encoding a first and a second protein of interest, for example, capsid protein L1, and L2, respectively. Each of the expression sequences may further comprises a promotor operably linked to the corresponding open reading frame. In certain embodiments, one of the expression sequences may include one promoter operably linked to more than one ORFs. For example, one of the expression sequences may include a promoter functionally linked to two different ORFs, one ORF encoding capsid protein L1, and the other ORF encoding capsid protein L2.

EXAMPLES

Unless specified otherwise, ingredients described in the examples are commercially available from common chemical suppliers. Some abbreviations used in the examples section are expanded as follows: "mg": milligrams; "ng": nanograms; "pg": picograms; "fg": femtograms; "mL": milliliters; "mg/mL": milligrams per milliliter; "mM": millimolar; "mmol": millimoles; "pM": picomolar; "pmol": picomoles; "μL": microliters; "min.": minutes and "h.": hours.

Example 1: Stoichiometric Expression of
Adeno-Associated Virus (AAV) Capsid Proteins
from 1:1:10 RCA Mixtures Stoichiometric expression of VP1, VP2, and VP3 capsid proteins was demonstrated by mixing and supplementing RCA DNA at a 1:1:10 ratio in cell-free protein expression reactions as shown in FIG. 11. Minimalistic expression sequences separately-encoding VP1, VP2, and VP3 were designed in silico and synthesized in vitro (SEQ ID #1-#3).

```
                                       SEQ ID #1
CCGGGATCCTTCTTTAAATTAATACGACTCACTATAGGGAGACCACAACGG

TTTCCCTCTAGAAATAATTTTGTTTAACTTTAAGAAGGAGATATACATATG

GCTGCTGACGGATATCTGCCGGATTGGTTGGAAGATAACCTTAGCGAAGGT

ATACGAGAGTGGTGGGATTTGAAGCCAGGGGCACCAAAGCCGAAGGCAAAT

CAACAAAAGCAAGACGACGGACGTGGATTGGTGTTGCCGGGATATAAGTAT

TTGGGACCGTTTAACGGTCTTGATAAGGGCGAGCCAGTTAACGCAGCAGAC

GCTGCAGCATTAGAACACGATAAGGCATACGATCAACAACTTAAGGCGGGG

GATAACCCTTACCTTCGTTACAATCACGCTGACGCCGAGTTTCAAGAAAGG

TTGCAAGAAGATACGAGCTTTGGTGGTAACCTTGGACGAGCAGTGTTCCAA

GCTAAGAAGCGGGTCCTAGAGCCGTTTGGACTTGTTGAAGAAGGCGCAAAA

ACAGCACCTGGAAAGAAGAGACCGGTAGAGCAAAGCCCACAAGAGCCGGAT

AGCTCCAGCGGAATTGGAAAGACTGGACAACAGCCGGCAAAGAAGCGTCTG

AATTTTGGACAAACCGGTGATTCCGAGAGCGTACCAGATCCACAGCCGCTT

GGTGAGCCACCAGCTACACCAGCAGCTGTTGGCCCTACGACAATGGCAAGC

GGCGGTGGCGCACCAATGGCTGATAATAACGAAGGTGCAGACGGGGTTGGA

AACGCAAGCGGAAATTGGCATTGTGATAGCACGTGGCTTGGGGATCGTGTT

ATCACGACGTCAACGAGAACGTGGGCACTTCCGACGTATAACAACCACTTG

TACAAGCAAATTAGCTCGGCAAGTACGGGGGCAAGCAACGATAATCACTAC

TTTGGATATTCCACGCCGTGGGGATATTTTGATTTTAACCGCTTTCATTGT
```

16

```
CACTTTAGCCCGCGTGATTGGCAACGGCTTATCAACAATAATTGGGGATTT

CGACCGAAGCGGCTTAACTTCAAGCTCTTTAACATTCAGGTCAAAGAAGTA

ACCACGAACGACGGTGTAACGACGATCGCCAATAATCTTACGAGCACGGTG

CAAGTGTTTTCCGATTCTGAGTATCAACTTCCGTACGTCCTTGGTTCCGCA

CATCAAGGGTGTTTACCGCCTTTTCCGGCCGACGTTTTTATGATCCCGCAA

TACGGATACCTTACGCTAAATAACGGGTCCCAAGCAGTGGGAAGAAGCAGC

TTCTATTGCCTTGAATATTTTCCAAGCCAAATGCTTCGGACCGGAAATAAC

TTTACCTTTAGCTATACGTTTGAAGACGTGCCGTTTCATTCGTCATACGCA

CATAGCCAAAGCCTAGATCGCCTTATGAATCCGTTGATCGATCAGTACCTT

TACTATCTCAATCGCACGCAAAATCAAAGCGGATCAGCACAAAATAAAGAC

CTGCTGTTTAGCCGCGGATCTCCAGCTGGCATGAGCGTACAACCGAAGAAT

TGGCTTCCGGGACCCTGCTATAGGCAACAACGCGTAAGTAAGACGAAGACG

GATAACAACAATAGCAACTTTACGTGGACAGGGGCTTCGAAGTACAATCTT

AACGGAAGGGAATCCATTATTAACCCTGGCACAGCTATGGCTAGCCACAAA

GACGATAAAGATAAGTTCTTTCCGATGTCCGGCGTCATGATTTTCGGAAAA

GAGTCCGCAGGTGCATCGAATACGGCACTTGATAACGTAATGATCACGGAC

GAAGAAGAGATAAAGGCTACGAATCCGGTCGCAACAGAGCGATTCGGAACG

GTTGCGGTAAATCTTCAATCGAGCAGCACAGATCCGGCAACTGGCGACGTC

CACGTTATGGGCGCACTTCCCGGCATGGTCTGGCAAGATAGGGACGTGTAC

CTTCAGGGACCGATTTGGGCTAAGATACCGCATACAGACGGACATTTTCAC

CCAAGTCCGCTTATGGGGGGATTTGGATTAAAGCACCCGCCGCCGCAAATA

CTCATAAAGAACACACCGGTGCCAGCAAATCCGCCGGCAGAGTTTAGTGCA

ACGAAGTTTGCAAGCTTTATCACACAATACAGCACGGGACAAGTAAGCGTA

GAGATCGAGTGGGAATTGCAAAAAGAGAATAGCAAGCGCTGGAATCCCGAA

GTGCAATATACGTCCAACTACGCGAAGAGCGCAAACGTTGATTTCACGGTC

GATAACAACGGACTTTATACGGAACCGCGTCCGATTGGAACGAGATATTTG

ACGCGACCGCTTTAATAACTAGCATAACCCCTTGGGGCCTCTAAACGGGTC

TTGAGGGGTTTTTTGCTGCAGAGATCTCCG
```

```
                                       SEQ ID #2
CCGGGATCCTTCTTTAAATTAATACGACTCACTATAGGGAGACCACAACGG

TTTCCCTCTAGAAATAATTTTGTTTAACTTTAAGAAGGAGATATACATATG

GCACCTGGAAAGAAGCGACCGGTTGAGCAATCTCCGCAAGAGCCGGATAGC

TCCAGCGGAATTGGAAAGACTGGACAACAACCGGCCAAGAAGCGATTGAAT

TTTGGACAAACGGGGGATTCCGAGAGTGTGCCTGATCCACAACCACTTGGC

GAGCCACCAGCAACACCAGCTGCAGTTGGCCCGACAACAATGGCATCTGGC

GGCGGCGCACCAATGGCTGATAACAACGAAGGGGCAGACGGTGTTGGAAAC

GCAAGCGGAAATTGGCATTGTGATTCGACGTGGCTTGGTGATAGGGTCATA

ACGACAAGCACGCGAACGTGGGCATTACCCACGTATAACAATCACCTCTAC

AAGCAAATTAGCAGCGCTAGCACTGGTGCATCGAACGATAACCACTACTTT

GGGTATAGCACACCGTGGGGATATTTCGATTTTAATCGGTTTCACTGCCAT

TTTAGCCCAAGGGATTGGCAACGTCTTATCAACAATAACTGGGGATTTAGG
```

-continued

CCTAAGCGCCTTAATTTCAAGCTGTTTAACATTCAGGTCAAAGAAGTAACG

ACGAACGACGGGGTGACGACGATCGCAAATAATCTTACGTCCACGGTGCAA

GTTTTTAGCGATAGCGAGTATCAATTACCGTACGTGCTTGGAAGCGCACAT

CAAGGTTGTCTTCCACCGTTTCCGGCAGACGTCTTTATGATTCCGCAATAC

GGATACCTTACGCTTAATAACGGAAGCCAAGCTGTAGGTCGGTCTAGCTTT

TACTGCCTTGAATACTTTCCGTCACAAATGCTTCGTACCGGAAACAACTTT

ACGTTTAGCTACACGTTTGAAGACGTGCCGTTTCACAGCTCGTACGCACAT

TCACAAAGCCTTGATCGCCTTATGAATCCGCTTATCGATCAATACCTCTAT

TATCTAAACCGGACGCAGAACCAATCGGGATCGGCACAAACAAAGATTTG

TTGTTTAGTCGCGGCAGTCCGGCTGGCATGAGCGTACAACCGAAGAATTGG

TTGCCGGGTCCTTGTTATCGTCAACAACGCGTAAGCAAGACGAAGACAGAT

AACAATAACAGCAATTTTACTTGGACGGGGGCATCCAAGTATAATCTGAAC

GGACGTGAATCCATCATAAACCCCGGCACAGCTATGGCAAGCCACAAAGAC

GATAAAGATAAGTTCTTTCCGATGTCCGGCGTTATGATCTTTGGAAAAGAA

TCAGCTGGGGCAAGTAATACGGCGCTTGATAACGTCATGATAACCGACGAA

GAAGAGATCAAGGCAACGAATCCGGTCGCAACGGAACGTTTTGGAACCGTT

GCGGTCAATCTTCAATCCAGCAGCACAGATCCGGCAACTGGCGACGTACAC

GTAATGGGCGCACTTCCTGGCATGGTGTGGCAAGATAGAGACGTGTACCTT

CAAGGGCCGATTTGGGCAAAGATACCGCATACGGACGGACACTTTCATCCA

TCCCCACTTATGGGTGGATTTGGACTTAAGCACCCGCCACCGCAAATTCTT

ATAAAGAACACGCCGGTACCAGCTAATCCGCCGGCTGAGTTTAGCGCAACC

AAGTTTGCAAGCTTTATCACGCAATATTCCACGGGACAGGTAAGCGTTGAG

ATCGAGTGGGAACTTCAAAAAGAGAATAGCAAGCGCTGGAATCCGGAAGTC

CAGTATACATCCAATTACGCGAAGAGCGCAAACGTCGATTTCACGGTGGAT

AATAACGGACTATACACGGAACCGAGACCGATTGGAACAAGGTATTTGACG

CGACCGCTTTAATAACTAGCATAACCCCTTGGGGCCTCTAAACGGGTCTTG

AGGGGTTTTTTGCTGCAGAGATCTCCG

SEQ ID #3
CCGGGATCCTTCTTTAAATTAATACGACTCACTATAGGGAGACCACAACGG

TTTCCCTCTAGAAATAATTTTGTTTAACTTTAAGAAGGAGATATACATATG

GCATCTGGCGGCGGCGCACCAATGGCAGATAATAACGAAGGTGCAGACGGG

GTTGGTAACGCTTCCGGAAATTGGCACTGTGATAGCACGTGGCTTGGTGAT

CGTGTGATCACAACAAGCACACGAACGTGGGCCTTACCGACGTACAACAAT

CACTTGTACAAGCAAATCAGCAGCGCATCCACAGGGGCATCTAACGATAAC

CACTATTTCGGATACAGCACGCCGTGGGGATATTTTGATTTTAACCGGTTT

CACTGCCATTTTAGTCCCCGCGATTGGCAAAGACTGATCAACAACAATTGG

GGATTTCGTCCGAAGCGACTTAATTTCAAGCTGTTCAACATACAAGTCAAA

GAAGTGACGACGAACGACGGGGTTACGACGATAGCAAATAACCTAACGAGC

ACGGTGCAAGTATTTAGCGATAGCGAGTATCAACTTCCGTACGTACTTGGA

TCAGCACATCAAGGGTGCCTTCCACCGTTTCCGGCAGACGTTTTTATGATT

CCGCAATACGGATACCTTACGTTGAATAACGGAAGCCAAGCAGTTGGAAGG

-continued

TCCAGCTTCTACTGTCTTGAATACTTTCCCAGCCAAATGCTTCGCACTGGA

AACAACTTTACCTTCAGCTATACATTTGAAGACGTGCCGTTTCATAGTAGC

TACGCTCATAGCCAAAGCCTTGATCGACTTATGAATCCGCTTATTGATCAA

TACCTGTATTACCTCAATCGCACACAGAATCAATCCGGATCGGCACAAAAC

AAAGATTTGCTCTTTAGCCGCGGCTCACCAGCTGGCATGTCCGTTCAACCG

AAGAATTGGCTTCCTGGACCGTGTTATCGTCAACAAAGGGTCTCCAAGACG

AAGACGGATAACAACAACAGCAATTTTACGTGGACGGGTGCGAGTAAGTAC

AATCTTAACGGACGCGAGAGCATTATTAATCCTGGCACAGCAATGGCTAGC

CACAAAGACGATAAAGATAAGTTTTTCCCGATGTCCGGCGTCATGATTTTT

GGAAAAGAGAGTGCAGGTGCATCGAATACGGCACTAGATAACGTAATGATC

ACGGACGAAGAAGAAATCAAGGCCACGAATCCTGTAGCAACGGAAAGGTTT

GGAACGGTTGCGGTGAATTTGCAAAGCAGCTCCACAGATCCAGCTACCGGC

GACGTTCACGTAATGGGCGCATTACCCGGCATGGTCTGGCAAGATCGAGAC

GTATATCTTCAAGGTCCGATCTGGGCTAAGATTCCACATACTGACGGACAC

TTTCATCCAAGCCCTCTTATGGGTGGATTTGGACTTAAGCATCCGCCGCCG

CAAATTCTCATCAAGAATACGCCGGTGCCGGCAAATCCACCAGCAGAGTTT

AGCGCAACCAAGTTTGCTAGCTTTATCACGCAATATTCGACGGGACAAGTG

AGCGTCGAGATAGAGTGGGAACTTCAGAAAGAGAACAGCAAGCGGTGGAAT

CCGGAAGTACAGTATACGAGCAATTACGCAAAGAGCGCAAACGTCGATTTT

ACCGTCGATAACAACGGGCTTTATACAGAGCCGAGACCGATAGGTACGCGG

TATCTTACGCGTCCGCTTTAATAACTAGCATAACCCCTTGGGGCCTCTAAA

CGGGTCTTGAGGGGTTTTTTGCTGCAGAGATCTCCG

Each expression sequence comprises a T7 promoter and T7 gene 10 leader ribosomal binding site for initiating cell-free mRNA transcription and protein translation, respectively. Double-stranded DNA encoding minimalistic expression sequences were digested with BamHI and BglII to create complementary overhangs for intra-molecular ligation into DNA mini-circles, followed by exonuclease treatment (ExoI, ExoIII) to digest any remaining non-circular DNA. Rolling-circle amplification (RCA) was then used to generate high molecular weight, hyper-branched concatemers consisting essentially of tandem repeats of each minimalistic expression sequence. As provided herein, RCA may be performed as disclosed in U.S. Pat. Nos. 10,077,459 and 9,938,568, the disclosures of which are incorporated by reference herein for all purposes. RCA provides a benefit of an easy, economical, and robust option to fulfill coupled in vitro transcription and translation reactions. RCA reagents, including water, reaction buffer, 40 μM primer, and 20 ng/μL phi29 DNA polymerase, were pre-cleaned of contaminating DNA prior to the addition of ligated mini-circle template and 400 μM dNTPs. Amplification was performed using hexamer primers having the sequence +N+N(atN)(atN)(atN)*N (AT hexamer), and 10 μM alpha-S-dATP was included in the reaction to thioate the resulting RCA product. RCA products were quantified using Quant-It™ Picogreen® dsDNA Assay Kit (ThermoFisher Inc) from a total RCA reaction volume of 100 μL, and then applied directly to cell-free protein expression reactions with no intermediate purification. To achieve stoichiometric expression of VP1, VP2, and VP3, individual RCA products were mixed at a mass ratio of 1:1:10 in Expressway™ extract (ThermoFisher Inc) for a total DNA content of 0.5 μg per 50 μL reaction. For control purposes, VP1, VP2, and VP3 (approximately 82 kD, 66 kD, and 60 kD respectively) were expressed in separate cell-free reactions by adding 0.5 μg of respective RCA DNA into 50 μL ExpressWay reactions. FluoroTect™ GreenLYS in vitro Translation Label (Promega) was added to all cell-free expression reactions to randomly-label nascent lysine residues (via anticodon UUU tRNA) with a fluorescent BODIPY-FL label. All cell-free expression reactions were incubated at 30° C. for 6 hours in an Eppendorf Thermo-Mixer (1200 rpm) and then analyzed by SDS-PAGE to visualize all BODIPY-labeled translation products by in-gel fluorescence using a Typhoon Variable Mode Imager (GE Healthcare). The data presented in FIG. 1 demonstrates stoichiometric expression of VP1, VP2, and VP3 capsid protein as prescribed by the 1:1:10 ratio of RCA DNA supplied to the cell-free protein expression reaction. In certain embodiments, RCA product encoding assembly-activation protein (AAP) and expressing at a 1:1:1:10 ratio (relative to VP1, VP2, VP3) may be used to strengthen viral capsid assembly and folding. Alternatively, RCA mixtures encoding VP3 and AAP may be sufficient to drive stoichiometric expression of virus-like particles in vitro.

Example 2: Stoichiometric Expression of Immunoglobulin Chains from 1:2 RCA Mixtures Stoichiometric expression of immunoglobulin heavy and light chains is demonstrated using two different RCA nucleic acid concatemer products. Minimalistic expression sequences separately-encoding IgG heavy and light chains were designed in silico and synthesized in vitro (SEQ ID #4-#5).

```
                                       SEQ ID #4
CCGGGATCCCAGTGAATTGTAATACGACTCACTATAGGGCGAATTAATTCC

GGTTATTTTCCACCATATTGCCGTCTTTTGGCAATGTGAGGGCCCGGAAAC

CTGGCCCTGTCTTCTTGACGAGCATTCCTAGGGGTCTTTCCCCTCTCGCCA

AAGGAATGCAAGGTCTGTTGAATGTCGTGAAGGAAGCAGTTCCTCTGGAAG

CTTCTTGAAGACAAACAACGTCTGTAGCGACCCTTTGCAGGCAGCGGAACC

CCCCACCTGGCGACAGGTGCCTCTGCGGCCAAAAGCCACGTGTATAAGATA

CACCTGCAAAGGCGGCACAACCCCAGTGCCACGTTGTGAGTTGGATAGTTG

TGGAAAGAGTCAAATGGCTCACCTCAAGCGTATTCAACAAGGGGCTGAAGG

ATGCCCAGAAGGTACCCCATTGTATGGGATCTGATCTGGGGCCTCGGTGCA

CATGCTTTACATGTGTTTAGTCGAGGTTAAAAAACGTCTAGGCCCCCCGAA

CCACGGGGACGTGGTTTTCCTTTGAAAAACACGATGATAATATGGCCACAA

CCAAGTGGGTCACCTTCATCTCCCTGCTGTTCCTCTTCTCGTCTGCCTACT

CCGACATTCAAATGACACAGTCGCCGTCCTCCCTGTCCGCGTCCGTGGGTG

ATCGGGTCACCATTACTTGCCGGGCGTCGCAGGGCATCAGAAACTACCTGG

CCTGGTACCAGCAGAAGCCCGGCAAGGCACCTAAGCTCCTTATCTACGCGG

CCAGCACACTTCAGAGCGGCGTGCCGTCAAGGTTCTCGGGGTCCGGATCAG

GCACCGACTTCACTCTGACTATTAGCAGCCTGCAGCCGGAGGACGTGGCCA

CCTACTACTGCCAACGCTACAACAGAGCTCCCTACACGTTTGGTCAAGGCA
```

```
                                     -continued
CCAAAGTGGAGATCAAGCGCACCGTGGCCGCCCCCTCGGTGTTCATCTTTC

CACCTTCCGACGAGCAGCTGAAGTCAGGAACTGCCTCCGTGGTCTGCCTGC

TGAACAACTTCTATCCGCGCGAGGCTAAGGTGCAGTGGAAGGTCGACAACG

CACTCCAGAGCGGAAACTCCCAGGAGTCCGTGACCGAACAGGACTCCAAGG

ATAGCACCTACTCACTCTCGTCCACCCTGACTTTGAGCAAGGCCGACTACG

AAAAGCATAAGGTCTACGCCTGCGAAGTGACCCACCAGGGACTGTCCTCCC

CTGTGACCAAGTCCTTCAATCGGGGGGAGTGTTAATAACATCTGACTGAAA

AAAAAAAGTTTAAACACTAGTCCGCTGAGCAATAACTAGCATAACCCCTT

GGGGCCTCTAAACGGGTCTTGAGGGGTTTTTTGCTGCAGAGATCTCCG

SEQ ID #5
CCGGGATCCCAGTGAATTGTAATACGACTCACTATAGGGCGAATTAATTCC

GGTTATTTTCCACCATATTGCCGTCTTTTGGCAATGTGAGGGCCCGGAAAC

CTGGCCCTGTCTTCTTGACGAGCATTCCTAGGGGTCTTTCCCCTCTCGCCA

AAGGAATGCAAGGTCTGTTGAATGTCGTGAAGGAAGCAGTTCCTCTGGAAG

CTTCTTGAAGACAAACAACGTCTGTAGCGACCCTTTGCAGGCAGCGGAACC

CCCCACCTGGCGACAGGTGCCTCTGCGGCCAAAAGCCACGTGTATAAGATA

CACCTGCAAAGGCGGCACAACCCCAGTGCCACGTTGTGAGTTGGATAGTTG

TGGAAAGAGTCAAATGGCTCACCTCAAGCGTATTCAACAAGGGGCTGAAGG

ATGCCCAGAAGGTACCCCATTGTATGGGATCTGATCTGGGGCCTCGGTGCA

CATGCTTTACATGTGTTTAGTCGAGGTTAAAAAACGTCTAGGCCCCCCGAA

CCACGGGGACGTGGTTTTCCTTTGAAAAACACGATGATAATATGGCCACAA

CCAAGTGGGTCACCTTCATCTCCCTGCTGTTTCTGTTCTCCTCCGCATACT

CGGAAGTCCAACTTGTGGAGTCCGGAGGAGGCCTGGTGCAGCCTGGACGCA

GCCTGAGACTGTCGTGTGCTGCGTCCGGATTCACTTTTGACGATTACGCTA

TGCATTGGGTCAGACAGGCCCCCGGGAAGGGGCTCGAGTGGGTGTCCGCCA

TCACTTGGAACAGCGGACACATCGACTACGCTGATTCTGTGGAGGGCCGCT

TCACTATCTCGCGGGACAACGCCAAGAACTCCCTGTACCTTCAAATGAATT

CCCTGCGGGCCGAGGATACTGCTGTGTACTACTGCGCCAAGGTGTCCTACC

TGTCCACTGCGTCGTCACTCGACTACTGGGGCCAGGGCACGCTGGTCACCG

TGTCCAGCGCGTCCACCAAGGGTCCGAGCGTGTTCCCGCTTGCCCCGTCAT

CGAAGTCTACCTCGGGCGGCACCGCCGCCCTCGGTTGCCTCGTCAAGGATT

ACTTCCCGGAGCCCGTGACTGTGTCCTGGAATAGCGGCGCCCTGACCTCGG

GAGTGCACACATTCCCGGCGGTGCTGCAGTCAAGCGGTTTGTACTCCCTGT

CGTCCGTCGTGACCGTGCCTAGCTCATCCCTGGGGACCCAGACCTACATTT

GCAACGTGAACCACAAGCCTTCCAACACCAAGGTCGACAAGAAGGTGGAGC

CCAAGTCGTGCGACAAGACCCATACCTGCCCTCCGTGCCCGGCCCCTGAGT

TGCTCGGGGGACCTTCCGTGTTCCTGTTCCCGCCGAAGCCTAAGGATACTC

TTATGATTAGCAGGACCCCCGAAGTGACCTGTGTGGTGGTGGACGTCAGCC

ACGAGGACCCCGAAGTCAAGTTCAATTGGTACGTGGACGGCGTGGAGGTCC

ATAACGCCAAGACTAAGCCAAGGGAGGAGCAGTATAACAGCACTTACCGGG

TGGTGTCAGTGCTGACCGTGCTGCATCAGGACTGGCTCAACGGCAAAGAGT
```

-continued

```
ACAAGTGCAAGGTGTCCAACAAGGCCCTGCCCGCACCCATTGAGAAGACCA

TTAGCAAGGCCAAGGGACAGCCACGGGAACCACAGGTGTACACCCTTCCCC

CATCCCGCGACGAACTGACTAAGAACCAAGTGTCCCTCACCTGTCTCGTGA

AGGGATTCTACCCGAGCGACATCGCAGTCGAGTGGGAATCGAACGGCCAGC

CCGAGAACAACTACAAGACGACTCCTCCGGTGCTGGACTCCGACGGTTCCT

TCTTCCTGTACTCCAAGCTGACCGTGGACAAGAGCCGCTGGCAGCAGGGCA

ACGTGTTCAGCTGCTCTGTTATGCACGAAGCCTTGCACAACCACTACACAC

AGAAGTCACTCTCCCTGTCGCCCGGCAAGTAATAACATCTGACTGAAAAAA

AAAAAGTTTAAACACTAGTCCGCTGAGCAATAACTAGCATAACCCCTTGGG

GCCTCTAAACGGGTCTTGAGGGGTTTTTTGCTGCAGAGATCTCCG
```

The expression sequences included a T7 promoter and an internal ribosome entry site (IRES) from Encephalomyocarditis virus (EMCV) for initiating cell-free mRNA transcription and protein translation, respectively. Double-stranded DNA encoding minimalistic expression sequences were digested with BamHI and BglII to create complementary overhangs for intra-molecular ligation into DNA minicircles, followed by exonuclease treatment (ExoI, ExoIII) to digest any remaining non-circular DNA. Rolling-circle amplification (RCA) was then used to generate high molecular weight, hyper-branched concatemers consisting essentially of tandem repeats of each minimalistic expression sequence. RCA and quantification was performed as disclosed in Example 1. RCA products were quantified using Quant-It™ Picogreen® dsDNA Assay Kit (ThermoFisher Inc) from a total RCA reaction volume of 100 μL, and then purified by ethanol precipitation. To achieve stoichiometric expression, individual RCA products encoding light chain and heavy chain were mixed at a mass ratio of 1:2, respectively, in 1-Step Human Coupled IVT extract (ThermoFisher Inc) for a total DNA content of 125 ng per 25 μL reaction. For control purposes, individual light- and heavy-chains (approximately 26 kD and 52 kD respectively) were expressed in separate cell-free reactions by adding 125 ng of respective RCA DNA into 25 μL 1-Step reactions. Fluoro-Tect™ GreenLYS in vitro Translation Label (Promega) was added to all cell-free expression reactions to randomly-label nascent lysine residues (via anticodon UUU tRNA) with a fluorescent BODIPY-FL label. The data presented in FIG. 12 demonstrates stoichiometric expression of light and heavy chain polypeptides as prescribed by the ratio of RCA DNA supplied to the cell-free protein expression reaction. The cell-free protein expression reaction may be further augmented by increasing the microsome content of the extract to encourage signal-peptide processing and disulfide bond-formation of the final IgG molecule.

Example 3: Formulation of RCA Mixtures for Functional AAV Virus Production

Figure 13:
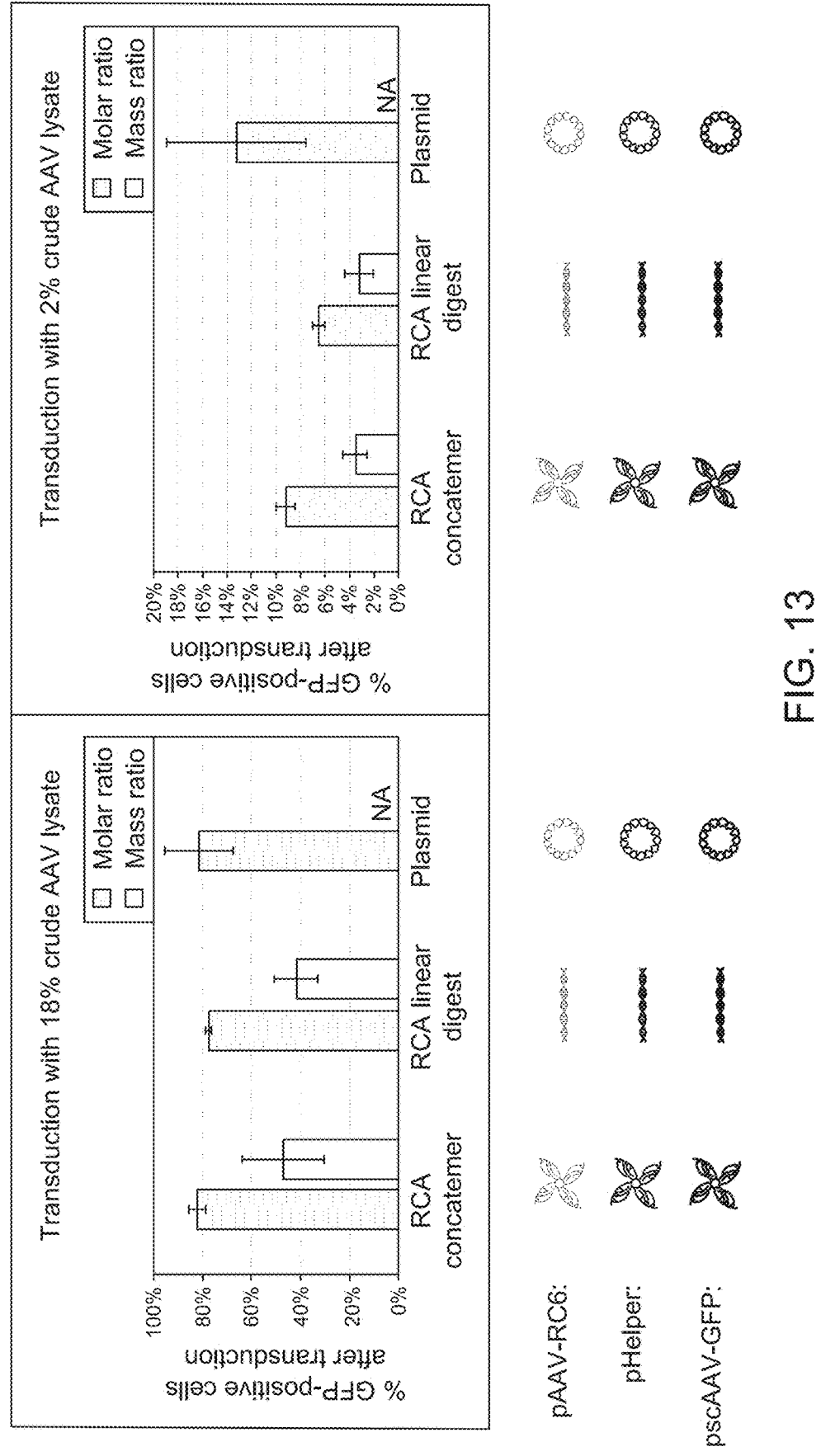
FIG. 13 is a bar graph demonstrating AAV production from intact rolling circle amplification-generated concatemers, rolling circle amplification-generated linear digests, and plasmids transfected into naïve cells at different concentrations (18% and 2%), according to embodiments of the present disclosure.
Figure 14:
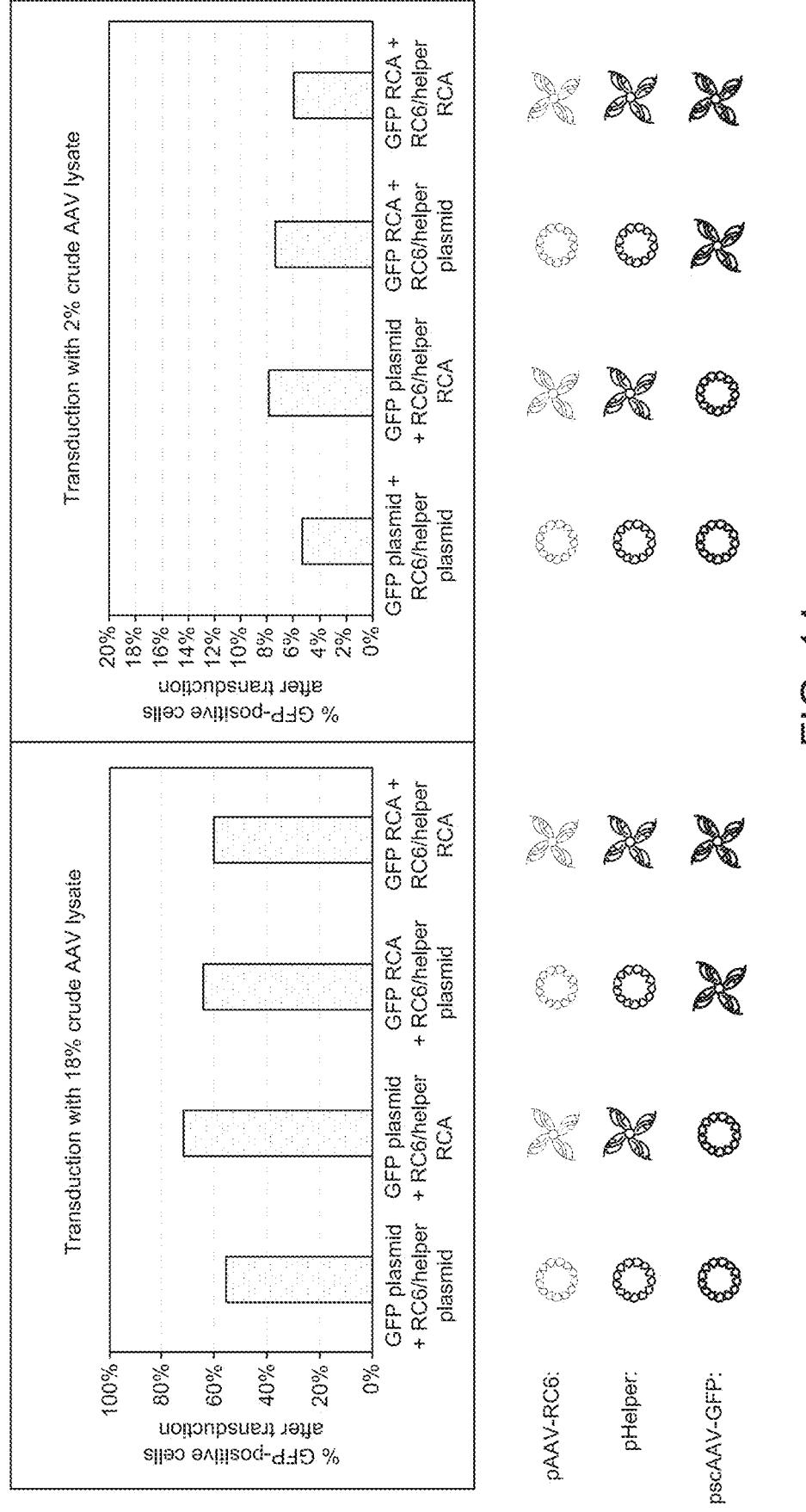
FIG. 14 is a bar graph demonstrating AAV production from mixed concatemer and plasmid expression product sources, according to embodiments of the present disclosure.

Recombinant AAV manufacturing generally involves simultaneous transfection of 3 different plasmids (Rep/Cap, Helper, and a packaged DNA transgene) into HEK293T producer cells. Transient transfection practices are used when manufacturing viral vectors for clinical trials because therapeutic virus can be produced rapidly at high yield, with generally higher titers (without significant pre-optimization) from anchorage-dependent producer cells compared to suspension-adapted cells. However, scale-up manufacturing of AAV is limited by the lead-time and expense of manufacturing plasmid DNA. Here, efficient production of functional AAV virus vector was shown by formulating and transfecting mixtures of RCA DNA (encoding Rep/Cap, Helper, and a GFP transgene) at 1:1:1 ratios in HEK293T cells. Plasmids encoding Rep/Cap (pAAV-RC6, Agilent Genomics), Helper (pHelper, Agilent Genomics), and a packaged DNA transgene (pscAAV-GFP, Cell Biolabs) were amplified using RCA, performed and quantified as disclosed herein, to generate high molecular weight, hyper-branched concatemers comprising tandem repeats of each plasmid. To generate AAV particles, individual RCA products were mixed at either mass or molar ratios of 1:1:1 and 4 μg of total DNA was transfected into HEK239T cells using DharmaFECT kB reagent. For control purposes, 4 μg of plasmid DNA or linear digests of RCA DNA (after ScaI endonuclease cleavage of concatemers into double-stranded monomers) were transfected into HEK293T cells at similar 1:1:1 ratios. DNA mixtures were pre-incubated with DharmaFECT for 10 minutes at room temperature prior to incubating with HEK293T cells for approximately 20 hours, followed by feeding transfected cells with fresh media. AAV crude lysates were collected three days post-transfection by harvesting and washing the cells prior to conducting 4 freeze-thaw cycles (via dry ice/ethanol bath at approximately −72° C. followed by warming in a 37° C. water bath). Cell debris was removed by centrifugation (10,000 g×10 min) and AAV crude lysates were incubated with naïve HEK293T cells at two different final concentrations (18% and 2%) in fresh media. Three days post-transduction, GFP-positive cells were quantified by flow cytometry against appropriate controls for proper gating. The data summarized in FIG. 13 demonstrate equivalent AAV production from intact RCA concatemers relative to plasmid DNA. Less virus was generated at 1:1:1 mass ratios of RCA DNA compared to 1:1:1 molar ratios of RCA DNA using both concatemeric and digested forms. Ratiometric comparison revealed that 1:1:1 DNA mass ratios reduce the relative amount of the longest coding DNA within the DNA mixture; therefore, it is likely that pHelper DNA was limiting for virus production. In subsequent experiments, individual RCA DNA was mixed with individual plasmids to evaluate 1:1:1 molar combinations by transfection. In all cases, concatemeric RCA DNA efficiently cooperated with plasmid DNA to generate comparable amounts of AAV virus, as shown in FIG. 14.

Example 4: Formulation of RCA Mixtures for Functional Lentivirus Production

Figure 15:
FIG. 15 is a bar graph demonstrating lentivirus production from mixed concatemer and plasmid expression product sources, according to embodiments of the present disclosure.

Efficient production of functional lentivirus was demonstrated by formulating and transfecting mixtures of RCA DNA (separately encoding VSV-G envelope, Gag/Pol, Rev, and a GFP mRNA) at stoichiometric ratios in HEK293T cells. Plasmids encoding Gag/Pol (pLP1, Invitrogen), Rev (pLP2, Invitrogen), VSV-G envelope (pLP3, Invitrogen), and a packaging GFP mRNA (pLenti-GFP, Cell Biolabs) were amplified by RCA, performed and quantified as disclosed herein, to generate high molecular weight, hyper-branched concatemers comprising tandem repeats of each plasmid. Amplification was performed using hexamer primers having the sequence +N+N(atN)(atN)(atN)*N (AT hexamer), and 10 μM alpha-S-dATP was optionally included in the pLenti-GFP reaction to thioate the resulting RCA product. To generate lentivirus, individual RCA products were mixed at a molar ratio of 1:1:1:1 and ~3 μg of total DNA was transfected into HEK239T cells using DharmaFECT kB reagent. For control purposes, approximately 3 μg of circular plasmid or linearized digests of plasmid (after Seal or PvuI endonuclease cleavage) were transfected into HEK293T cells at similar 1:1:1:1 ratios. DNA mixtures were pre-incubated with DharmaFECT for 10 minutes at room temperature prior to incubating with HEK293T cells for approximately 20 hours, followed by replacing with fresh media. Spent media (containing lentivirus) was collected three days post-transfection and filtered through a 0.2 μm syringe filter prior to transducing naïve HEK293T cells in the presence of 5 μg/mL polybrene. Approximately 24 hrs after viral transduction, cells were fed with fresh media and incubated for an additional 2-3 days. Cells were then collected (3-4 days post transduction) and GFP-positive cells were quantified by flow cytometry against appropriate gating controls. The data summarized in FIG. 15 demonstrate non-optimized lentivirus production from intact RCA concatemers. The particular stoichiometric mixtures of RCA products or plasmids are examples, and lentivirus can be produced using alternative stoichiometric mixtures. For example, higher ratios of RCA DNA mixtures with plasmid DNA, specifically 1:3:3:3 and 3:1:1:1 molar combinations of pLenti-GFP:LP1:LP2:LP3 respectively, were tested. In either case, concatemeric RCA DNA efficiently cooperated with plasmid DNA to generate comparable amounts of lentivirus, as shown in FIG. 15.

Concatemer Generation and Expression Products of Concatemers

Provided herein are techniques for using concatemers (e.g., concatemers 16) to generate desired expression products, which may include one or more proteins or nucleic acids. The resultant expression products may be collected (e.g., purified, harvested) after expression and used as part of a treatment or therapy protocol for a subject. Embodiments of the disclosure include generating one or more expression products from concatemers as provided herein and treating a subject using the generated expression products. For example, the disclosed techniques may be used to generate viral vectors that encode a desired transgene. Accordingly, an expression product as provided herein may be part of a viral vector that includes a nucleic acid with an expression sequence encoding the desired transgene and that may be used as part of a gene therapy protocol in which the subject is treated with the viral vector. Because the transgene is selected based on the therapy needs of the subject, the transgene may be a variable or customizable component of a viral vector production system while other components of the viral vector production system are constant or less variable. Further, certain components of viral vectors may be selected based on desired tropism or patient characteristics. Accordingly, provided herein are kits that include premade or pre-produced portions of a viral vector production system that are constant or that are selected from a few possible options as well as reagents and precursor molecules to permit users to generate the customizable portions of the system.

In another embodiment, a custom antibody may be generated using the concatemer expression products. In another embodiment, a CRISPR/Cas9 system may be generated using the concatemer expression products. In another embodiment, virus-like particles may be generated using the concatemer expression products. While certain embodiments including expression of products related to gene editing, gene therapy, and custom molecules have been disclosed, it should be understood that the disclosed techniques may be used to generate suitable expression products for other applications. These include multi-subunit protein complexes (e.g. human DNA polymerase alpha is a complex of 4 different subunits in a 1:1:1:1 ratio), and enzyme combinations that can perform different steps of a biochemical pathway.

Throughout the specification, exemplification of specific terms should be considered as non-limiting examples. The singular forms "a", "an" and "the" include plural referents unless the context clearly dictates otherwise. Approximating language, as used herein throughout the specification and claims, may be applied to modify any quantitative representation that could permissibly vary without resulting in a change in the basic function to which it is related.

The present disclosure may use nucleic acid amplification techniques as part of a workflow to generate expression products. As used herein, the term "primer" refers to a short linear oligonucleotide that hybridizes to a target nucleic acid sequence (e.g., a DNA template to be amplified) to prime a nucleic acid synthesis reaction. The primer may be an RNA oligonucleotide, a DNA oligonucleotide, or a chimeric sequence. The primer may contain natural, synthetic, or modified nucleotides. Both the upper and lower limits of the length of the primer are empirically determined. The lower limit on primer length is the minimum length that is required to form a stable duplex upon hybridization with the target nucleic acid under nucleic acid amplification reaction conditions. Very short primers (usually less than 3 nucleotides long) do not form thermodynamically stable duplexes with target nucleic acid under such hybridization conditions. The upper limit is often determined by the possibility of having a duplex formation in a region other than the predetermined nucleic acid sequence in the target nucleic acid. Generally, suitable primer lengths are in the range of about 3 nucleotides long to about 40 nucleotides long.

As used herein, the term "random primer" refers to a mixture of primer sequences, generated by randomizing a nucleotide at any given location in an oligonucleotide sequence in such a way that the given location may consist of any of the possible nucleotides or their analogues (complete randomization). Thus the random primer is a random mixture of oligonucleotide sequences, consisting of every possible combination of nucleotides within the sequence. For example, a hexamer random primer may be represented by a sequence or $(N)_6$. A hexamer random DNA primer consists of every possible hexamer combinations of 4 DNA nucleotides, A, C, G and T, resulting in a random mixture comprising $4^6$ (4,096) unique hexamer DNA oligonucleotide sequences. Random primers may be effectively used to prime a nucleic acid synthesis reaction when the target nucleic acid's sequence is unknown or for performing a whole-genome amplification reaction. Random primers may also be effective in priming and producing double-stranded rolling circle amplification (RCA) product rather than single-stranded RCA product, depending on the concentration of primer.

As used herein, the term "nucleotide analogue" refers to compounds that are structurally analogous to naturally occurring nucleotides. The nucleotide analogue may have an altered phosphate backbone, sugar moiety, nucleobase, or combinations thereof. Nucleotide analogues may be a natural nucleotide, a synthetic nucleotide, a modified nucleotide, or a surrogate replacement moiety (e.g., inosine). Generally, nucleotide analogues with altered nucleobases confer, among other things, different base pairing and base stacking proprieties. As used herein, the term "LNA (Locked Nucleic Acid) nucleotide" refers to a nucleotide analogue, wherein the sugar moiety of the nucleotide contains a bicyclic furanose unit locked in a ribonucleic acid (RNA)-mimicking sugar conformation. The structural change from a deoxyribonucleotide (or a ribonucleotide) to the LNA nucleotide is limited from a chemical perspective, namely the introduction of an additional linkage between carbon atoms at the 2' position and 4' position (e.g., 2'-C, 4'-C-oxymethylene linkage; see, for example, Singh, S. K., et. al., Chem. Comm., 4, 455-456, 1998, or Koshkin, A. A., et. al., Tetrahedron, 54, 3607-3630, 1998)). The 2' and 4' position of the furanose unit in the LNA nucleotide may be linked by an O-methylene (e.g., oxy-LNA: 2'-O, 4'-C-methylene-β-D-ribofuranosyl nucleotide), an S-methylene (thio-LNA), or an NH-methylene moiety (amino-LNA), and the like. Such linkages restrict the conformational freedom of the furanose ring. LNA oligonucleotides display enhanced hybridization affinity toward complementary single-stranded RNA, and complementary single- or double-stranded DNA. The LNA oligonucleotides may induce A-type (RNA-like) duplex conformations. Nucleotide analogues having altered phosphate-sugar backbone (e.g., PNA, LNA) often modify, among other things, the chain properties such as secondary structure formation. A star (*) sign preceding a letter designation denotes that the nucleotide designated by the letter is a phosphorothioate modified nucleotide. For example, *N represents a phosphorothioate modified random nucleotide. A plus (+) sign preceding a letter designation denotes that the nucleotide designated by the letter is a LNA nucleotide. For example, +A represents an adenosine LNA nucleotide, and +N represents a locked random nucleotide (i.e., a random LNA nucleotide). As used herein, the term "phosphorothioated nucleotide" or "thioated nucleotide" refers to a nucleotide that has an altered phosphate backbone, wherein, the sugar moieties are linked by a phosphorothioate bond. In the phosphate backbone of an oligonucleotide sequence, the phosphorothioate bond contains a sulfur atom as a substitute for a non-bridging oxygen atom. This modification may render the internucleotide linkage resistant to nuclease degradation. The thioated nucleotide (thioated dNTPs) may include, but are not limited to, α-S-dGTP, α-S-dCTP, α-S-dATP, or α-S-dTTP.

As used herein, the term "rolling circle amplification (RCA)" refers to a nucleic acid amplification reaction that amplifies a circular nucleic acid template (e.g., single/double stranded DNA circles) via a rolling circle mechanism. Rolling circle amplification reaction is initiated by the hybridization of a primer to a circular, often single-stranded, nucleic acid template. The nucleic acid polymerase then extends the primer that is hybridized to the circular nucleic acid template by continuously progressing around the circular nucleic acid template to replicate the sequence of the nucleic acid template over and over again (rolling circle mechanism). The rolling circle amplification typically produces concatemers comprising tandem repeat units of the circular nucleic acid template sequence. The rolling circle amplification may be a linear RCA (LRCA), exhibiting linear amplification kinetics (e.g., RCA using a single, specific primer), or may be an exponential RCA (ERCA) exhibiting exponential amplification kinetics. Rolling circle amplification may also be performed using multiple primers (multiply primed rolling circle amplification or MPRCA) leading to hyper-branched concatemers. For example, in a double-primed RCA, one primer may be complementary, as in the linear RCA, to the circular nucleic acid template, whereas the other may be complementary to the tandem repeat unit nucleic acid sequences of the RCA product. Consequently, the double-primed RCA may proceed as a chain reaction with exponential amplification kinetics featuring a cascade in series of multiple-hybridization, primer-extension, and strand-displacement events involving both the primers and both strands. This often generates a discrete set of concatemeric, double-stranded nucleic acid amplification products. The RCA may be performed in vitro under isothermal conditions using a suitable nucleic acid polymerase such as Phi29 DNA polymerase. Suitable polymerases possess strand displacement DNA synthesis ability. In certain embodiments, the rolling circle amplification may be performed using a random primer mixture comprising a nucleotide analogue.

As used herein, the term "rolling circle amplification (RCA) product" or "RCA product DNA" refers to a nucleic acid amplification product wherein a circular nucleic acid template (e.g., single/double stranded DNA circles) amplifies via a rolling circle amplification reaction mechanism. The template is of smaller size relative to the product of RCA. The rolling circle amplification typically produces concatemers comprising tandem repeat units of the circular nucleic acid template sequence. The rolling circle amplification product DNA may be generated by a linear RCA (LRCA), exhibiting linear amplification kinetics (e.g., RCA using a single, specific primer), or by an exponential RCA (ERCA) exhibiting exponential amplification kinetics. Rolling circle amplification product DNA may also be generated by using multiple primers (multiply primed rolling circle amplification or MPRCA), wherein the rolling circle amplification product DNA is hyper-branched concatemers. In a double-primed RCA, one primer may be complementary, as in the linear RCA, to the circular nucleic acid template, whereas the other may be complementary to the tandem repeat unit nucleic acid sequences of the RCA product DNA. The RCA product DNA may be generated by the RCA in vitro under isothermal conditions using a suitable nucleic acid polymerase such as Phi29 DNA polymerase.

DNA amplification techniques such as rolling circle amplification (RCA) can be employed to generate large quantities of high-quality DNA, starting from a circular nucleic acid template. Rolling circle amplification may produce a nucleic acid concatemer comprising tandem repeat units of the corresponding circular nucleic acid template. The nucleic acid concatemer may be a linear or a branched concatemer.

As used herein the term "nucleic acid concatemer" (e.g., a concatemer 16 as disclosed herein) refers to a nucleic acid molecule having tandem repeats or tandem repeat units of a nucleic acid sequence (e.g., an expression sequence 12). The terms "concatemer", "nucleic acid concatemer", and "DNA concatemer" may be used interchangeably throughout the disclosure. Concatemers may be single or double-stranded. As used herein, the term "double stranded concatemeric DNA" refers to a double stranded DNA molecule that contains multiple copies of the same DNA sequences linked in series. Concatemers generated from RCA may be larger than 1 kilobase (kb), larger than 10 kb, larger than 150 kb. In one embodiment, the concatemers may be in a range of 50 kb-150 kb. The size of the concatemer relates to the size of the starting template (e.g., template 14) and the number of tandem repeats, which may vary. Accordingly, an RCA performed on a template solution may generate a pool of concatemers having tandem repeats of the same sequence but with variable numbers of tandem repeats and, therefore, variable length. In certain embodiments, the nucleic acid concatemer may include a plurality of tandem repeat sequences, wherein each of the plurality of tandem repeat sequences includes an expression sequence encoding for an expression product.

In certain embodiments, the nucleic acid concatemer is a DNA concatemer. The DNA concatemer may be generated using a DNA mini-circle as a template, where the DNA mini-circle consists essentially of a minimalistic expression sequence. The resulting concatemer contains tandem repeats of the minimalistic expression sequence derived from the DNA mini-circle. In certain embodiments, the minimalistic expression sequence consisting essentially of a promoter, a cap-independent translation element, and an open reading frame. In certain embodiments, the nucleic acid concatemer comprises a modified nucleotide, a nucleotide analogue, or a combination thereof.

As used herein the term "expression sequence" or "repeat unit of expression sequence" (e.g., the expression sequence 12) refers to a DNA sequence that is competent for RNA and/or protein expression. Therefore, an expression product comprises protein, RNA, or a mixture thereof.

In certain embodiments, wherein protein expression is sought, the expression sequence may include an expression-competent unit that comprises an open reading frame (ORF) and a promotor operably linked to the open reading frame. In one embodiment, ORF may code for one or more proteins. The coded proteins may be the same or different. In some embodiments, an expression sequence may include one promoter operably linked to more than one ORF.

In certain embodiments, wherein RNA expression is sought, the expression sequence may include an RNA-expression competent unit that comprises at least one promoter and a transcription termination sequence.

The repeat unit of a sequence of a concatemer may include a promoter, an open reading frame, a ribosomal binding site, and a translational termination sequence. It may additionally contain sequences that do not materially affect the in vitro transcription and/or translation of the RCA product. For example, it may further include sequences such as a translational enhancer sequence, an insulator sequence, or a transcriptional termination sequence.

Numerous examples of suitable promoters are known in the art, including, for example, T7 RNA polymerase promoter sequences or promoter sequences derived from viruses such as CMV or SV40.

Likewise, numerous examples of suitable ribosomal binding sites are known in the art, including for examples internal ribosome entry sites (IRES), polyA tracts, species-independent translational leaders (SITS), Kozak consensus sequences, and Shine-Dalgarno sequences. The insulator sequence generally enhances the efficiency of ribosomal binding or translational initiation. Numerous examples of suitable insulator sequences exist in the art, including for example, sequences encoding poly-histidine tracts. In some embodiments the insulator sequence may be determined empirically by inserting spacer sequences around the ribosomal binding site or by optimizing or inserting codons within the N-terminus of the expressed protein. In certain embodiments, the expression sequence may comprise a polyA sequence, a transcriptional termination sequence, an insulator sequence, or a combination thereof.

In certain embodiments, the open reading frame of the expression sequence may include a codon-optimized sequence, a purification tag sequence, an amino-terminal peptide fusion sequence derived from an IRES, a sequence for protease cleavage or nucleotide cleavage, or combinations thereof. In some embodiments, the expression sequence comprises both coding and non-coding sequences.

The codon-optimized sequence of the open reading frame may enhance the rate or quality of translation of the RCA product. Codon optimization generally improves the protein expression by increasing the translational efficiency of a gene of interest. The functionality of a gene may also be increased by optimizing codon usage within the custom designed gene. In codon optimization embodiments, a codon of low frequency in a species may be replaced by a codon with high frequency, for example, a codon UUA of low frequency may be replaced by a codon CUG of high frequency for leucine. Codon optimization may increase mRNA stability and therefore modify the rate of protein translation or protein folding. Further, codon optimization may customize transcriptional and translational control, modify ribosome binding sites, or stabilize mRNA degradation sites.

The open reading frame of the expression sequence may comprise a purification tag sequence for purification of the expressed product (e.g. expressed protein). The tag sequence may be an affinity tag, tag for protease cleavage or combinations thereof. The affinity tag may be used for rapid purification and detection of recombinant proteins.

The open reading frame of the expression sequence may comprise an amino-terminal peptide fusion sequence derived from an IRES for enhanced ribosome recognition.

In some embodiments, the expression sequence contains a coding sequence, wherein the coding sequence codes for or generates a desired protein expression product in the eukaryotic cell. The coding sequence is a nucleic acid sequence containing a particular gene of interest. In general, the coding sequence comprises a promoter, and an open reading frame (ORF). The coding sequence may optionally include a cap-independent translation element (CITE). In some embodiments, the coding sequence further comprises a ribosomal binding site. The coding sequence may comprise a transcription terminator sequence located outside the open reading frame but within the expression sequence.

In one or more embodiments, each of the plurality of tandem repeat sequences comprises at least one expression sequence. In some embodiments, the at least one expression sequence comprises at least one coding sequence. In such embodiments, the at least one coding sequence of the at least one expression sequence comprises at least one promoter, and at least one open reading frame. In some embodiments, each of the plurality of tandem repeat sequences comprises two or more expression sequences. The two or more expression sequences including coding sequences may code for a same protein or different proteins. In some embodiments, the expression sequence includes at least one promoter that is functionally linked to at least one open reading frame. For example, in one aspect, in an expression sequence, one promoter is functionally linked to one open reading frame. In another aspect, in an expression sequence, one promoter is functionally linked to two different open reading frames. In some embodiments, the expression sequence may include two or more promoters functionally linked to two or more open reading frames.

An expression sequence may include a promoter operably linked to two different open reading frames, such as a first open reading frame and a second open reading frame, each of them coding a protein that is different from the other. In this example, a single promoter is functionally linked to two open reading frames via a cap-independent translation element. Each of the open reading frames includes translation start and translation stop sequences. A translational termination or stop sequence is required for an expression sequence, otherwise an infinite polyprotein may be synthesized, which is undesirable. However, a transcriptional stop codon may be optional for the first open reading frame leading to the generation of a polycistronic mRNA upon transcription. In such instances, the intervening sequences between the first and second open reading frames may be selected such that upon in vivo protein expression, even if a single polycistronic mRNA is produced, it can be translated to two different proteins. Synthesis of the first protein by translation of the first open reading frame may be followed by a ribosomal slippage to the second translation start sequence of the second open reading frame to initiate the synthesis of the second protein from the second open reading frame. This may be achieved by incorporating "self-cleaving sequences" between the first and second open reading frames. Suitable self-cleaving sequences such as viral P2A motif facilitates the creation of two or more proteins from one single mRNA.

In some embodiments, the expression sequence contains a non-coding sequence, wherein the non-coding sequence generates a desired RNA expression product. Such expression sequence does not contain any coding sequence. The non-coding sequence comprises a promoter and a transcription termination sequence. The non-coding sequence is generally devoid of an open reading frame. The expression sequence that contains a non-coding sequence is also referred to as an RNA expression sequence. In some embodiments, the expression sequence consists essentially of a noncoding sequence. In some other embodiments, the expression sequence includes both the coding and non-coding sequences, wherein the RNA can be generated from a non-coding sequence of an expression sequence. In such embodiments, a desired protein may also be subsequently generated from the coding sequence of the same expression sequence. In some embodiments, the generated RNA may be extracted from the eukaryotic cells for different downstream applications. In one embodiment, the extracted RNA may subsequently be packaged into a lentivirus system to deliver in another cell. The non-coding sequence may include, but is not limited to, a sequence for antisense RNA, a short interfering RNA (siRNA), a short hairpin RNA (shRNA), a microRNA (miRNA), a microRNA mimic, a transfer RNA (tRNA), a ribosomal RNA (rRNA), or combinations thereof. The non-coding sequence may also include CRISPR RNAs (tracrRNA, crRNA, sgRNA, or gRNA), small nuclear RNA (snRNA), small nucleolar RNA (snoRNA), Piwi interacting RNA (piRNA), telomerase RNA, spliceosome RNA, enhancer RNA, retrotransposons, X inactive specific transcript (Xist), RNAs encoded by RNA polymerase I and RNA polymerase III, or combinations thereof.

As noted, both the coding sequence and the non-coding sequence comprise a promoter. Any of the suitable promoters known in the art, including, for example, T7 RNA polymerase or CMV promoter sequences, may be used in the methods described herein. Likewise, any of suitable ribosomal binding sites known in the art, including but not limited to, IRES, polyA tracts, species-independent translational leaders (SITS), Kozak consensus sequences, and Shine-Dalgarno sequences may be used.

The open reading frame includes translation start and translation stop sequences. In some embodiments, the open reading frame comprises a codon-optimized sequence for enhancing translation. The open reading frame may comprise an amino-terminal peptide fusion sequence derived from an internal ribosome entry site (IRES) for enhanced ribosome recognition, a tag sequence for purification of the desired protein, or a combination thereof. The CITE may comprise an IRES, a translation enhancing element (TEE), or a combination thereof.

The desired protein may be purified by a tag sequence, wherein the tag sequence may be fusion tag for affinity purification, tag for protease cleavage or combinations thereof. The fusion tag for affinity purification may be used for rapid purification and detection of the expressed proteins. These tags are also referred as affinity tag. The affinity tag may include a polyhistidine tag, Glutathione S-transferase tag (GST), haemagglutinin (HA), myc (derived from c-myc gene product), FLAG (consisting of eight amino acids Asp-Tyr-Lys-Asp-Asp-Asp-Asp-Lys including an enterokinase-cleavage site) or combinations thereof. The fusion tags help in rapid purification or detection of the desired protein, however, the tags may not be considered to be permanent fixtures or domains of the recombinant proteins. Hence, removal of the fusion tag is often needed for highly analytical studies of recombinant protein structure and function. The tag for purification may be removed from the protein by using another type of tag, such as protease cleavage tag. The protease cleavage tag may be used to cleave a distinct peptide bond within a specific protein or peptide sequence. The protease cleavage tag may include, for example, PreScission™ Protease tag (GE Healthcare Life Sciences) or thrombin protease tag (GE Healthcare Life Sciences).

As noted, the open reading frame of the coding sequence may comprise a codon-optimized sequence, wherein the codon optimized sequence is generated by considering different factors, such as codon bias, contextual codon preference, and/or individual codon preference. The codon-optimized sequence of the open reading frame may enhance the rate or quality of translation of the RCA product. Codon optimization generally improves the protein expression from the coding sequence by increasing the translational efficiency of a gene of interest. The functionality of a gene may also be increased by optimizing codon usage within the custom designed gene. In codon optimization embodiments, a codon of low frequency in a species may be replaced by a codon with high frequency, for example, a codon UUA of low frequency may be replaced by a codon CUG of high frequency for leucine. Codon optimization may increase mRNA stability and therefore modify the rate of protein translation or protein folding. Further, codon optimization may customize transcriptional and translational control, modify ribosome binding sites, or stabilize mRNA degradation sites.

The transcription termination sequence is generally situated at the 3' end of a gene in a DNA template. The transcription termination sequence provides signal in the newly synthesized mRNA to initiate the process of releasing the mRNA from the transcriptional complex, which can also aid in effective translation of the desired protein product. The insulator sequence generally enhances the efficiency of ribosomal binding or translational initiation. Numerous examples of suitable insulator sequences that exist in the art may be used, including for example, sequences encoding poly-histidine tracts. In some embodiments, the insulator sequence may be determined empirically by inserting spacer sequences around the ribosomal binding site or by optimizing or inserting codons within the N-terminus of the expressed protein.

In some embodiments, the expression sequence comprises a coding sequence, a non-coding sequence, or a combination thereof. The coding sequence comprises a promoter, an open reading frame, and optionally a cap-independent translation element (CITE). The cap-independent translation element (CITE) of the coding sequence may be an internal ribosome entry site (IRES), a translation enhancing element (TEE), or a combination thereof. The open reading frame of the coding sequence may be codon-optimized for enhancing translation. The open reading frame may further comprise a tag sequence for purification of the desired protein, an amino-terminal peptide fusion sequence derived from an IRES for enhanced ribosome recognition, or a combination thereof. The expression sequence further comprises a polyA sequence, a transcriptional termination sequence, an insulator sequence, or a combination thereof.

In some embodiments, the expression sequence is a minimalistic expression sequence that is devoid of any extraneous sequences that are required for propagation of a plasmid in a host cell. The minimalistic expression sequence for expressing a desired protein includes, at the minimum, a promoter, a ribosomal binding site, and a translational termination sequence. The minimalistic expression sequence for expressing a desired RNA includes, at the minimum, a promoter, a ribosomal binding site, and a translational termination sequence. In some embodiments, the double-stranded RCA product DNA consists essentially of tandem repeats of a minimalistic expression sequence. In such embodiments, the expression sequence may additionally contain sequences that do not materially affect the in vivo protein expression or RNA expression using the RCA product DNA as a template. For example, it may further include sequences such as a translational enhancer sequence, an insulator sequence, or a transcriptional termination sequence. The minimalistic expression sequence of the RCA product DNA excludes any extraneous sequences, such as antibiotic selection gene, or any other accessory sequences that are required for cloning, selection, screening and/or replication in a host cell. The RCA product may be a linear or a branched concatemer containing tandem repeats of the minimalistic expression sequence. The minimalistic expression sequence of the RCA product DNA may be derived from a DNA mini-circle that includes only minimalistic expression sequence.

The double-stranded concatemeric DNA may further comprise an inosine-containing nucleotide, a Locked Nucleic Acid (LNA) nucleotide, a Peptide Nucleic Acid (PNA) nucleotide, 2-amino-deoxyadenosine, 2-thio-deoxythymidine, a polycation nucleotide, or a combination thereof. In some embodiments, the modified nucleotides, such as inosine-containing nucleotide, a Locked Nucleic Acid (LNA) nucleotide, a Peptide Nucleic Acid (PNA) nucleotide, 2-amino-deoxyadenosine, 2-thio-deoxythymidine, a polycation nucleotide are part of a primer sequence that is employed for rolling circle amplification.

A variety of methods may be used to prepare a DNA mini-circle template for use with the disclosed techniques. In some embodiments, a linear DNA template may be circularized to generate a DNA mini-circle template. In one example embodiment, the circularization of the linear DNA template may be effected by an enzymatic reaction, for example, by incubation with a ligation enzyme such as DNA ligase. In some embodiments, the terminal ends of the linear DNA template are hybridized to a nucleic acid sequence such that the terminal ends come in close proximity. Incubating with a ligation enzyme may then effect the circularization of the hybridized linear DNA template to generate a DNA mini-circle. Suitable DNA mini-circle template may also be generated by PCR amplification of a portion of a larger DNA (for example, a genomic DNA, or a DNA from a DNA library) using appropriate PCR primers, followed by circularization of the PCR product. DNA mini-circle may also be generated by chemical synthesis of suitable linear oligonucleotides followed by circularization of the synthesized oligonucleotide. In some embodiments, the synthesized linear oligonucleotides may consist essentially of minimalistic expression sequence and achieve circularization via DNA ligase to generate DNA mini-circle.

Provided herein are expression systems (e.g., expression system 20) that may be used to generate expression products (e.g., expression products 26). The expression system 20 may be a cell-based expression system (e.g., mammalian, insect) or a cell-free expression system. Examples of cell-based expression systems include CHO, NIH3T3, BHK, HepG2, and HEK 293 cell-based expression systems.

In certain embodiments, "cell-free expression system" refers to an in vitro transcription and translation system. Cell-free expression generally encompasses two modes: (1) mRNA and protein are made in a single reaction or (2) mRNA is made in a first reaction and the resulting mRNA product is added to a second, separate translation reaction. The RCA product derived from a DNA mini-circle may be utilized for either modes, (1) or (2). For example, in one embodiment, the RCA product may be provided to a "coupled in vitro transcription-translation reaction", wherein the RCA product DNA is converted to an mRNA and the mRNA is simultaneously expressed to a protein in one reaction mixture containing both the ability to produce RNA and protein. In another embodiment, the RCA product may be provided to a "linked transcription-translation reaction", wherein the RCA product DNA is first converted to mRNA and the mRNA is added separately to a translation reaction mixture to express a protein. In certain embodiments, the concatemer is provided to a cell-free expression system unprocessed (or without any further processing). In one embodiment, the concatemer is added to the cell-free system directly after amplification such as RCA. The term "further processing" is meant to include an act of restriction digestion, ligation, or combinations thereof, of the concatemer. However, in some embodiments, the RCA product may be separated (e.g., by precipitation) to remove salts or any other contaminants, such as primers or smaller fragmented DNA from the reaction medium before proceeding for cell-free expression, for example, using a eukaryotic cell-extract.

The cell-free expression system may be an in vitro translation, cell-free protein expression, cell-free translation, or cell-free protein synthesis system. A non-limiting example of the cell-free expression system is a eukaryotic cell-free expression system. In certain embodiments, the concatemeric DNA may be immobilized onto a substrate prior to subjecting the concatemeric DNA to a cell-free expression system. The substrate-immobilized concatemeric DNA may be recovered from the cell-free expression system after expressing the recombinant product in vitro; and re-used for a subsequent in vitro transcription and translation reaction.

The concatemeric DNA (e.g., double-stranded concatemeric DNA) may be delivered to a eukaryotic cell expression system by any method, including but not limited to, electroporation, sonoporation, impalefection, transduction, optical transfection, magnetofection, nucleofection, hydro-dynamic delivery, heat shock-mediated gene delivery, nanoparticle mediated gene-gun delivery, calcium phosphate-mediated delivery, cationic polymer-mediated delivery, or liposome-mediated delivery.

In some embodiments, a eukaryotic cell comprising an exogeneous, double-stranded concatemeric DNA comprising a plurality of tandem repeat sequences is provided. In one embodiment, each of the plurality of tandem repeat sequences comprises a phosphorothioated nucleotide, wherein a ratio of phosphorothioated nucleotides to total nucleotides is at least 1:1600. The exogeneous, double-stranded concatemeric DNA employed for transfection into eukaryotic cells to generate the said cell may be an unprocessed or a processed RCA product DNA. The eukaryotic cell may be a protozoa, a yeast cell, an insect cell, or a mammalian cell.

Technical effects of the disclosed embodiments include improved expression of desired expression products using nucleic acid concatemers having sizes that are not typically associated with robust transfection and production of a desired expression product. Further, while the concatemers may include an unknown or variable number of tandem repeats of the expression sequence, different concatemers may nonetheless may be co-expressed ratiometrically, e.g., based on molar ratio, to generate predicate and robust ratios of the resultant expression products. The present disclosure demonstrates that concatemers with nucleic acid expression sequences for one or more desired expression products may replace and/or be used in conjunction with traditional expression techniques, such as plasmids, to produce desired expression products that have improved purity and robust co-expression. Further, nucleic acid concatemers may be used to generate more complex structures or assemblies in which multiple co-expressed products associate with one another.

The foregoing examples are illustrative of some features of the disclosure, and are selected embodiments from a manifold of all possible embodiments. While only certain features have been illustrated, and described herein, one skilled in the art, given the benefit of this disclosure, will be able to make modifications/changes to optimize the parameters. The foregoing embodiments are therefore to be considered in all respects as illustrative rather than limiting the embodiments described herein. Where ranges have been supplied, those ranges are inclusive of all sub-ranges there between.

This written description uses examples, including the best mode, and also to enable any person skilled in the art to practice the disclosed embodiments, including making and using any devices or systems and performing any incorporated methods. The patentable scope is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal languages of the claims.

---

The invention claimed is:

1. A method comprising:

formulating a concatemer mixture comprising at least a first nucleic acid concatemer and a second nucleic acid concatemer having a predefined ratio to one another, wherein the first nucleic acid concatemer comprises tandem repeats of a first nucleic acid sequence and wherein the second nucleic acid concatemer comprises tandem repeats of a second nucleic acid sequence; and co-expressing the concatemer mixture to generate a first expression product from the first nucleic acid sequence and a second expression product from the second nucleic acid sequence, wherein the first nucleic acid concatemer, the second nucleic acid concatemer, or both are over 10 kb in length, wherein the ratio of first expression product to the second expression product is proportional to the predefined ratio of the first nucleic acid concatemer to the second nucleic acid concatemer in the concatemer mixture, and wherein the molar ratio of the first concatemer to the second concatemer is between 1:1 and 1:10.

2. The method of claim 1, comprising generating the first nucleic acid concatemer and the second nucleic acid concatemer using rolling circle amplification.

3. The method of claim 2, comprising using the rolling circle amplification to amplify circular or plasmid DNA to generate the first nucleic acid concatemer and/or the second nucleic acid concatemer.

4. The method of claim 3, wherein the first tandem repeats and/or the second tandem repeats are tandem repeats of the circular or plasmid DNA.

5. The method of claim 1, comprising transfecting cultured cells with the concatemer mixture to cause the co-expressing or wherein the co-expressing is in a cell-free expression system.

6. The method of claim 1, comprising collecting the first expression product and the second expression product.

7. The method of claim 1, wherein one or both of the first nucleic acid concatemer or the second nucleic acid concatemer is unprocessed before the co-expressing.

8. The method of claim 1, wherein the first expression product is an envelope or packing protein of a virus and the second expression product comprises a transgene of the virus, wherein the first expression product and the second expression product form a viral vector for delivering the transgene.

9. The method of claim 1, wherein the first expression product is a nucleic acid product and the second expression product is a protein product.

10. The method of claim 9, wherein the first expression product forms a complex with the second expression product.

11. The method of claim 1, wherein the first expression product acts on a third nucleic acid concatemer in the concatemer mixture.

12. A method comprising:

formulating a mixture comprising at least a first nucleic acid concatemer, a second nucleic acid concatemer, and a third nucleic acid concatemer in a predefined ratio, wherein each of the nucleic acid concatemers comprises tandem repeats of two or more nucleic acid sequences; and co-expressing the concatemer mixture to generate a first expression product, a second expression product, and a third expression product from each nucleic acid concatemer in the mixture, wherein the first nucleic acid concatemer, the second nucleic acid concatemer, the third nucleic acid concatemer, or any combination thereof are over 10 kb in length, wherein the molar ratio of the the first expression product, the second expression product, and the third expression product is proportional to the predefined molar ratio of the first nucleic acid concatemer, the second nucleic acid concatemer, and the third nucleic acid concatemer in the concatemer mixture, and wherein the molar ratio of the first concatemer to the second concatemer to the third concatemer is C1:C2:$C_n$, where C1, C2, and $C_n$ each is between 1 and 10.

13. The method of claim 12, wherein the nucleic acid sequence of an individual concatemer in the concatemer mixture comprises a plurality of expression sequences that, when expressed to generate the two or more expression products, generate a plurality of proteins.

14. The method of claim 12, wherein the nucleic acid sequence of an individual concatemer in the concatemer mixture comprises a plurality of expression sequences that, when expressed to generate the two or more expression products, generate a mix comprising at least one protein expression product and at least one nucleic acid expression product.

15. A method, comprising:

amplifying at least one template comprising a first nucleic acid sequence using strand-displacement rolling circle amplification to a generate a first concatemer comprising tandem repeats of the first nucleic acid sequence;

contacting the first concatemer with a second concatemer comprising tandem repeats of a second nucleic acid sequence to form a concatemer mixture having a predefined ratio of the first nucleic acid concatemer to the second nucleic acid concatemer; and co-expressing the concatemer mixture to generate a first expression product from the first nucleic acid sequence and a second expression product from the second nucleic acid sequence, wherein a ratio of the first expression product to the second expression product is proportional to the predefined ratio of the first nucleic acid concatemer to the second nucleic acid concatemer in the concatemer mixture, wherein the molar ratio of the first concatemer to the second concatemer is between 1:1 and 1:10, and wherein the first concatemer, the second concatemer, or both are over 10 kb in length.

16. The method of claim 15, comprising allowing the first expression product to form a complex with the second expression product.

17. The method of claim 15, wherein the first expression product and the second expression product comprise different viral products from a same virus.

18. The method of claim 17, wherein the same virus is an adenovirus or a lentivirus.

19. The method of claim 15, wherein the first expression product comprises a viral mRNA and the second expression product comprises a plurality of viral packaging proteins.

20. A method comprising:

formulating a mixture comprising at least one nucleic acid concatemer and at least one plasmid having a predefined ratio to one another, wherein the at least one nucleic acid concatemer comprises tandem repeats of a first nucleic acid sequence and wherein the at least one plasmid comprises a second nucleic acid sequence; and co-expressing the mixture to generate a first expression product from the first nucleic acid sequence and a second expression product from the second nucleic acid sequence, wherein the molar ratio of the first concatemer to the plasmid is between 1:1 and 1:10, wherein the first nucleic acid concatemer is over 10 kb in length, and wherein the co-expression of the first expression product and the second expression product is ratiometric based on the predefined ratio.

21. The method of claim 1, wherein the co-expression of the first expression product and the second expression product is ratiometric based on the predefined ratio.

22. The method of claim 12, wherein the co-expression of the first expression product, the second expression product, and the third expression product is ratiometric based on the predefined ratio.

* * * * *

SEQUENCE LISTING

```
<160> NUMBER OF SEQ ID NOS: 5

<210> SEQ ID NO 1
<211> LENGTH: 2376
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 1
ccgggatcct tctttaaatt aatacgactc actataggga gaccacaacg gtttccctct      60
agaaataatt ttgtttaact ttaagaagga gatatacata tggctgctga cggatatctg     120
ccggattggt tggaagataa ccttagcgaa ggtatacgag agtggtggga tttgaagcca     180
ggggcaccaa agccgaaggc aaatcaacaa aagcaagacg acggacgtgg attggtgttg     240
ccgggatata agtatttggg accgtttaac ggtcttgata agggcgagcc agttaacgca     300
gcagacgctg cagcattaga acacgataag gcatacgatc aacaacttaa ggcggggggat     360 aacccttacc ttcgttacaa tcacgctgac gccgagtttc aagaaaggtt gcaagaagat     420
acgagctttg gtggtaacct tggacgagca gtgttccaag ctaagaagcg ggtcctagag     480
ccgtttggac ttgttgaaga aggcgcaaaa acagcacctg gaaagaagag accggtagag     540
caaagcccac aagagccgga tagctccagc ggaattggaa agactggaca acagccggca     600
aagaagcgtc tgaattttgg acaaaccggt gattccgaga gcgtaccaga tccacagccg     660
cttggtgagc caccagctac accagcagct gttggcccta cgacaatggc aagcggcggt     720
ggcgcaccaa tggctgataa taacgaaggt gcagacgggg ttggaaacgc aagcggaaat     780
tggcattgtg atagcacgtg gcttggggat cgtgttatca cgacgtcaac gagaacgtgg     840
gcacttccga cgtataacaa ccacttgtac aagcaaatta gctcggcaag tacgggggca     900
agcaacgata atcactactt tggatattcc acgccgtggg gatattttga ttttaaccgc     960
tttcattgtc actttagccc gcgtgattgg caacggctta tcaacaataa ttggggattt    1020
cgaccgaagc ggcttaactt caagctcttt aacattcagg tcaaagaagt aaccacgaac    1080
gacggtgtaa cgacgatcgc caataatctt acgagcacgg tgcaagtgtt ttccgattct    1140
```

-continued

```
gagtatcaac ttccgtacgt ccttggttcc gcacatcaag ggtgtttacc gccttttccg      1200
gccgacgttt ttatgatccc gcaatacgga taccttacgc taaataacgg gtcccaagca      1260
gtgggaagaa gcagcttcta ttgccttgaa tattttccaa gccaaatgct tcggaccgga      1320
aataacttta cctttagcta tacgtttgaa gacgtgccgt ttcattcgtc atacgcacat      1380
agccaaagcc tagatcgcct tatgaatccg ttgatcgatc agtaccttta ctatctcaat      1440
cgcacgcaaa tcaaagcgg atcagcacaa aataaagacc tgctgtttag ccgcggatct        1500
ccagctggca tgagcgtaca accgaagaat tggcttccgg gaccctgcta taggcaacaa      1560
cgcgtaagta agacgaagac ggataacaac aatagcaact ttacgtggac aggggcttcg      1620
aagtacaatc ttaacggaag ggaatccatt attaaccctg gcacagctat ggctagccac      1680
aaagacgata aagataagtt ctttccgatg tccggcgtca tgattttcgg aaaagagtcc      1740
gcaggtgcat cgaatacggc acttgataac gtaatgatca cggacgaaga agagataaag      1800
gctacgaatc cggtcgcaac agagcgattc ggaacggttg cggtaaatct tcaatcgagc      1860
agcacagatc cggcaactgg cgacgtccac gttatgggcg cacttcccgg catggtctgg      1920
caagataggg acgtgtacct tcagggaccg atttgggcta agataccgca tacagacgga      1980
cattttcacc caagtccgct tatggggga tttggattaa agcacccgcc gccgcaaata       2040
ctcataaaga acacaccggt gccagcaaat ccgccggcag agtttagtgc aacgaagttt      2100
gcaagcttta tcacacaata cagcacggga caagtaagcg tagagatcga gtgggaattg      2160
caaaaagaga atagcaagcg ctggaatccc gaagtgcaat atacgtccaa ctacgcgaag      2220
agcgcaaacg ttgatttcac ggtcgataac aacggacttt atacggaacc gcgtccgatt      2280
ggaacgagat atttgacgcg accgctttaa taactagcat aacccccttgg ggcctctaaa     2340 cgggtcttga ggggtttttt gctgcagaga tctccg                                2376
```

<210> SEQ ID NO 2
<211> LENGTH: 1965
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 2

```
ccgggatcct tctttaaatt aatacgactc actatagggga gaccacaacg gtttccctct        60
agaaataatt ttgtttaact ttaagaagga gatatacata tggcacctgg aaagaagcga      120
ccggttgagc aatctccgca agagccggat agctccagcg gaattggaaa gactggacaa      180
caaccggcca agaagcgatt gaattttgga caaacggggg attccgagag tgtgcctgat      240
ccacaaccac ttggcgagcc accagcaaca ccagctgcag ttggcccgac aacaatggca      300
tctggcggcg gcgcaccaat ggctgataac aacgaagggg cagacggtgt tggaaacgca      360
agcggaaatt ggcattgtga ttcgacgtgg cttggtgata gggtcataac gacaagcacg      420
cgaacgtggg cattacccac gtataacaat cacctctaca agcaaattag cagcgctagc      480
actggtgcat cgaacgataa ccactacttt gggtatagca caccgtgggg atatttcgat      540
tttaatcggt ttcactgcca tttttagccca aggattggc aacgtcttat caacaataac      600 tggggatta ggcctaagcg ccttaatttc aagctgttta acattcaggt caaagaagta      660
acgacgaacg acgggggtgac gacgatcgca ataatctta cgtccacggt gcaagttttt      720
agcgatagcg agtatcaatt accgtacgtg cttggaagcg cacatcaagg ttgtcttcca      780
```

```
ccgtttccgg cagacgtctt tatgattccg caatacggat accttacgct taataacgga      840
agccaagctg taggtcggtc tagctttac tgccttgaat actttccgtc acaaatgctt      900
cgtaccggaa acaactttac gtttagctac acgtttgaag acgtgccgtt tcacagctcg      960
tacgcacatt cacaaagcct tgatcgcctt atgaatccgc ttatcgatca atacctctat     1020
tatctaaacc ggacgcagaa ccaatcggga tcggcacaaa acaaagattt gttgtttagt     1080
cgcggcagtc cggctggcat gagcgtacaa ccgaagaatt ggttgccggg tccttgttat     1140
cgtcaacaac gcgtaagcaa gacgaagaca gataacaata acagcaattt tacttggacg     1200
ggggcatcca agtataatct gaacggacgt gaatccatca taaacccggg cacagctatg     1260
gcaagccaca aagacgataa agataagttc tttccgatgt ccggcgttat gatctttgga     1320
aaagaatcag ctggggcaag taatacggcg cttgataacg tcatgataac cgacgaagaa     1380
gagatcaagg caacgaatcc ggtcgcaacg gaacgttttg gaaccgttgc ggtcaatctt     1440
caatccagca gcacagatcc ggcaactggc gacgtacacg taatgggcgc acttcctggc     1500
atggtgtggc aagatagaga cgtgtacctt caagggccga tttgggcaaa gataccgcat     1560
acggacggac actttcatcc atccccactt atgggtggat ttggacttaa gcacccgcca     1620
ccgcaaattc ttataaagaa cacgccggta ccagctaatc cgccggctga gtttagcgca     1680
accaagtttg caagctttat cacgcaatat tccacgggac aggtaagcgt tgagatcgag     1740
tgggaacttc aaaaagagaa tagcaagcgc tggaatccgg aagtccagta tacatccaat     1800
tacgcgaaga gcgcaaacgt cgatttcacg gtggataata acggactata cacggaaccg     1860
agaccgattg gaacaaggta tttgacgcga ccgctttaat aactagcata accccttggg     1920
gcctctaaac gggtcttgag gggtttttttg ctgcagagat ctccg                    1965
```

```
<210> SEQ ID NO 3
<211> LENGTH: 1770
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 3
ccgggatcct tctttaaatt aatacgactc actataggga gaccacaacg gtttccctct       60
agaaataatt ttgtttaact ttaagaagga gatatacata tggcatctgg cggcggcgca      120
ccaatggcag ataataacga aggtgcagac ggggttggta acgcttccgg aaattggcac      180
tgtgatagca cgtggcttgg tgatcgtgtg atcacaacaa gcacacgaac gtgggcctta      240
ccgacgtaca acaatcactt gtacaagcaa atcagcagcg catccacagg ggcatctaac      300
gataaccact atttcggata cagcacgccg tggggatatt ttgattttaa ccggtttcac      360
tgccatttta gtccccgcga ttggcaaaga ctgatcaaca acaattgggg atttcgtccg      420
aagcgactta atttcaagct gttcaacata caagtcaaag aagtgacgac gaacgacggg      480
gttacgacga tagcaaataa cctaacgagc acggtgcaag tatttagcga tagcgagtat      540
caacttccgt acgtacttgg atcagcacat caagggtgcc ttccaccgtt tccggcagac      600
gtttttatga ttccgcaata cggatacctt acgttgaata acggaagcca agcagttgga      660
aggtccagct tctactgtct tgaatacttt cccagccaaa tgcttcgcac tggaaacaac      720
tttaccttca gctatacatt tgaagacgtg ccgtttcata gtagctacgc tcatagccaa      780
agccttgatc gacttatgaa tccgcttatt gatcaatacc tgtattacct caatcgcaca      840
```

-continued

```
cagaatcaat ccggatcggc acaaaacaaa gatttgctct ttagccgcgg ctcaccagct      900
ggcatgtccg ttcaaccgaa gaattggctt cctggaccgt gttatcgtca acaaagggtc      960
tccaagacga agacggataa caacaacagc aattttacgt ggacgggtgc gagtaagtac     1020
aatcttaacg gacgcgagag cattattaat cctggcacag caatggctag ccacaaagac     1080
gataaagata agtttttccc gatgtccggc gtcatgattt ttggaaaaga gagtgcaggt     1140
gcatcgaata cggcactaga taacgtaatg atcacggacg aagaagaaat caaggccacg     1200
aatcctgtag caacggaaag gtttggaacg gttgcggtga atttgcaaag cagctccaca     1260
gatccagcta ccgcgacgt tcacgtaatg ggcgcattac ccggcatggt ctggcaagat     1320
cgagacgtat atcttcaagg tccgatctgg gctaagattc acatactga cggacacttt     1380 catccaagcc ctcttatggg tggatttgga cttaagcatc cgccgccgca aattctcatc     1440
aagaatacgc cggtgccggc aaatccacca gcagagttta gcgcaaccaa gtttgctagc     1500
tttatcacgc aatattcgac gggacaagtg agcgtcgaga tagagtggga acttcagaaa     1560
gagaacagca agcggtggaa tccggaagta cagtatacga gcaattacgc aaagagcgca     1620
aacgtcgatt ttaccgtcga taacaacggg ctttatacag agccgagacc gataggtacg     1680
cggtatctta cgcgtccgct ttaataacta gcataacccc ttggggcctc taaacgggtc     1740 ttgagggggtt ttttgctgca gagatctccg                                      1770
```

```
<210> SEQ ID NO 4
<211> LENGTH: 1374
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 4
```

```
ccgggatccc agtgaattgt aatacgactc actatagggc gaattaattc cggttatttt       60
ccaccatatt gccgtctttt ggcaatgtga gggcccggaa acctggccct gtcttcttga      120
cgagcattcc taggggtctt tcccctctcg ccaaaggaat gcaaggtctg ttgaatgtcg      180
tgaaggaagc agttcctctg gaagcttctt gaagacaaac aacgtctgta gcgaccctt      240 gcaggcagcg gaacccccca cctggcgaca ggtgcctctg cggccaaaag ccacgtgtat      300
aagatacacc tgcaaaggcg gcacaacccc agtgccacgt tgtgagttgg atagttgtgg      360
aaagagtcaa atggctcacc tcaagcgtat tcaacaaggg gctgaaggat gcccagaagg      420
taccccattg tatgggatct gatctggggc ctcggtgcac atgctttaca tgtgtttagt      480
cgaggttaaa aaacgtctag gccccccgaa ccacggggac gtggtttccc tttgaaaaac      540
acgatgataa tatggccaca accaagtggg tcaccttcat ctccctgctg ttcctcttct      600
cgtctgccta ctccgacatt caaatgacac agtcgccgtc ctccctgtcc gcgtccgtgg      660
gtgatcgggt caccattact tgccgggcgt cgcagggcat cagaaactac ctggcctggt      720
accagcagaa gcccggcaag gcacctaagc tccttatcta cgcggccagc acacttcaga      780
gcggcgtgcc gtcaaggttc tcggggtccg gatcaggcac cgacttcact ctgactatta      840
gcagcctgca gccggaggac gtggccacct actactgcca acgctacaac agagctccct      900
acacgtttgg tcaaggcacc aaagtggaga tcaagcgcac cgtggccgcc ccctcggtgt      960
tcatctttcc accttccgac gagcagctga agtcaggaac tgcctccgtg gtctgcctgc     1020
tgaacaactt ctatccgcgc gaggctaagg tgcagtggaa ggtcgacaac gcactccaga     1080
```

-continued

```
gcggaaactc ccaggagtcc gtgaccgaac aggactccaa ggatagcacc tactcactct    1140
cgtccaccct gactttgagc aaggccgact acgaaaagca taaggtctac gcctgcgaag    1200
tgacccacca gggactgtcc tcccctgtga ccaagtcctt caatcggggg gagtgttaat    1260
aacatctgac tgaaaaaaaa aaagtttaaa cactagtccg ctgagcaata actagcataa    1320 cccccttgggg cctctaaacg ggtcttgagg ggttttttgc tgcagagatc tccg          1374
```

```
<210> SEQ ID NO 5
<211> LENGTH: 2085
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 5
```

```
ccgggatccc agtgaattgt aatacgactc actatagggc gaattaattc cggttatttt      60
ccaccatatt gccgtctttt ggcaatgtga gggcccggaa acctggccct gtcttcttga     120
cgagcattcc taggggtctt tcccctctcg ccaaaggaat gcaaggtctg ttgaatgtcg     180
tgaaggaagc agttcctctg gaagcttctt gaagacaaac aacgtctgta gcgacccttt     240
gcaggcagcg gaaccccca cctggcgaca ggtgcctctg cggccaaaag ccacgtgtat      300
aagatacacc tgcaaaggcg gcacaacccc agtgccacgt tgtgagttgg atagttgtgg     360
aaagagtcaa atggctcacc tcaagcgtat tcaacaaggg gctgaaggat gcccagaagg     420
taccccattg tatgggatct gatctggggc ctcggtgcac atgctttaca tgtgtttagt     480
cgaggttaaa aaacgtctag gccccccgaa ccacggggac gtggttttcc tttgaaaaac     540
acgatgataa tatggccaca accaagtggg tcaccttcat ctccctgctg tttctgttct     600
cctccgcata ctcggaagtc caacttgtgg agtccggagg aggcctggtg cagcctggac     660
gcagcctgag actgtcgtgt gctgcgtccg gattcacttt tgacgattac gctatgcatt     720
gggtcagaca ggccccccgggg aagggggctcg agtgggtgtc cgccatcact tggaacagcg     780
gacacatcga ctacgctgat tctgtggagg gccgcttcac tatctcgcgg gacaacgcca     840
agaactccct gtaccttcaa atgaattccc tgcgggccga ggatactgct gtgtactact     900
gcgccaaggt gtcctacctg tccactgcgt cgtcactcga ctactgggggc cagggcacgc     960 tggtcaccgt gtccagcgcg tccaccaagg gtccgagcgt gttcccgctt gccccgtcat    1020
cgaagtctac ctcgggcggc accgccgccc tcggttgcct cgtcaaggat acttcccgg     1080 agcccgtgac tgtgtcctgg aatagcggcg ccctgacctc gggagtgcac acattcccgg    1140
cggtgctgca gtcaagcggt ttgtactccc tgtcgtccgt cgtgaccgtg cctagctcat    1200
ccctggggac ccagacctac atttgcaacg tgaaccacaa gccttccaac accaaggtcg    1260
acaagaaggt ggagcccaag tcgtgcgaca gacccatac ctgccctccg tgccggccc     1320 ctgagttgct cggggggacct tccgtgttcc tgttcccgcc gaagcctaag gatactctta    1380
tgattagcag gaccccgaa gtgacctgtg tggtggtgga cgtcagccac gaggaccccg    1440
aagtcaagtt caattggtac gtggacggcg tggaggtcca taacgccaag actaagccaa    1500
gggaggagca gtataacagc acttaccggg tggtgtcagt gctgaccgtg ctgcatcagg    1560
actggctcaa cggcaaagag tacaagtgca aggtgtccaa caaggccctg cccgcaccca    1620
ttgagaagac cattagcaag gccaagggggac agccacggga accacaggtg tacacccttc    1680
ccccatcccg cgacgaactg actaagaacc aagtgtccct cacctgtctc gtgaagggat    1740
```

```
tctacccgag cgacatcgca gtcgagtggg aatcgaacgg ccagcccgag aacaactaca    1800
agacgactcc tccggtgctg gactccgacg gttccttctt cctgtactcc aagctgaccg    1860
tggacaagag ccgctggcag cagggcaacg tgttcagctg ctctgttatg cacgaagcct    1920
tgcacaacca ctacacacag aagtcactct ccctgtcgcc cggcaagtaa taacatctga    1980
ctgaaaaaaa aaaagtttaa acactagtcc gctgagcaat aactagcata accccttggg    2040
gcctctaaac gggtcttgag gggttttttg ctgcagagat ctccg                   2085
```